United States Patent
Valbusa et al.

(10) Patent No.: US 12,324,648 B2
(45) Date of Patent: Jun. 10, 2025

(54) ASSISTING MEDICAL PROCEDURES WITH LUMINESCENCE IMAGES PROCESSED IN LIMITED INFORMATIVE REGIONS IDENTIFIED IN CORRESPONDING AUXILIARY IMAGES

(71) Applicant: SurgVision GmbH, Munich (DE)

(72) Inventors: Giovanni Valbusa, Colleretto Giacosa (IT); Adrian Taruttis, Munich (DE)

(73) Assignee: SurgVision GmbH, Munich (DE)

( * ) Notice: Subject to any disclaimer, the term of this patent is extended or adjusted under 35 U.S.C. 154(b) by 305 days.

(21) Appl. No.: 17/801,218

(22) PCT Filed: Feb. 19, 2021

(86) PCT No.: PCT/EP2021/054162
§ 371 (c)(1),
(2) Date: Aug. 19, 2022

(87) PCT Pub. No.: WO2021/165471
PCT Pub. Date: Aug. 26, 2021

(65) Prior Publication Data
US 2022/0409057 A1    Dec. 29, 2022

(30) Foreign Application Priority Data
Feb. 21, 2020 (EP) .................... 20158847

(51) Int. Cl.
*A61B 5/00* (2006.01)
*G06T 5/40* (2006.01)
(Continued)

(52) U.S. Cl.
CPC ............ *A61B 5/0071* (2013.01); *G06T 5/40* (2013.01); *G06T 5/92* (2024.01); *G06T 5/94* (2024.01);
(Continued)

(58) Field of Classification Search
CPC . A61B 5/0071; A61B 5/7267; A61B 2505/05; A61B 2576/00; A61B 5/02007;
(Continued)

(56) References Cited

U.S. PATENT DOCUMENTS 5,866,331 A * 2/1999 Singer .................. C12Q 1/6841
359/396
11,259,874 B1 * 3/2022 Landon .................. G16H 40/67
(Continued)

FOREIGN PATENT DOCUMENTS

EP    1347285 A1    9/2003
EP    3610779 A1    2/2020
(Continued)

OTHER PUBLICATIONS

International Searching Authority, "International Search Report and Written Opinion from PCT Application No. PCT/US2021/054162 dated May 28, 2018", pp. 1 through 22, Published in: EP.
(Continued)

*Primary Examiner* — Adil Partap S Virk
(74) *Attorney, Agent, or Firm* — Bryan A. Santarelli; FisherBroyles, LLP

(57) ABSTRACT

A solution is proposed for assisting a medical procedure. A corresponding method comprises acquiring a luminescence image (205F), based on a luminescence light, and an auxiliary image (205R), based on an auxiliary light different from this luminescence light, of a field of view (103); the field of view (103) contains a region of interest comprising a target body of the medical procedure (containing a luminescence substance) and one or more foreign objects. An auxiliary informative region (210Ri) representative of the region of interest without the foreign objects is identified in the auxiliary image (205R) according to its content, and a luminescence informative region (210Fi) is identified in the
(Continued)

luminescence image (205F) according to the auxiliary informative region (210Ri). The luminescence image (205F) is processed limited to the luminescence informative region (210Fi) for facilitating an identification of a representation of the target body therein. A computer program and a corresponding computer program product for implementing the method are also proposed. Moreover, a computing device for performing the method and an imaging system comprising it are proposed. A medical procedure based on the same solution is further proposed.

24 Claims, 10 Drawing Sheets

(51) Int. Cl.

| | | |
|---|---|---|
| *G06T 5/92* | (2024.01) | |
| *G06T 5/94* | (2024.01) | |
| *G06T 7/11* | (2017.01) | |
| *G06T 7/136* | (2017.01) | |
| *G06T 7/174* | (2017.01) | |
| *G06T 7/187* | (2017.01) | |
| *G06T 7/194* | (2017.01) | |
| *G06V 10/26* | (2022.01) | |
| *G06V 10/28* | (2022.01) | |
| *G06V 10/50* | (2022.01) | |
| *G06V 10/60* | (2022.01) | |
| *G06V 10/764* | (2022.01) | |
| *G06V 10/77* | (2022.01) | |

(52) U.S. Cl.
CPC .............. *G06T 7/11* (2017.01); *G06T 7/136* (2017.01); *G06T 7/174* (2017.01); *G06T 7/187* (2017.01); *G06T 7/194* (2017.01); *G06V 10/267* (2022.01); *G06V 10/28* (2022.01); *G06V 10/507* (2022.01); *G06V 10/60* (2022.01); *G06V 10/764* (2022.01); *G06V 10/7715* (2022.01); *A61B 5/7267* (2013.01); *A61B 2505/05* (2013.01); *A61B 2576/00* (2013.01); *G06T 2207/10064* (2013.01); *G06T 2207/20084* (2013.01); *G06T 2207/30004* (2013.01); *G06T 2207/30096* (2013.01); *G06V 2201/034* (2022.01)

(58) Field of Classification Search
CPC .... G06T 5/40; G06T 5/92; G06T 5/94; G06T 7/11; G06T 7/136; G06T 7/174; G06T 7/187; G06T 7/194; G06T 2207/10064; G06T 2207/20084; G06T 2207/30004; G06T 2207/30096; G06T 2207/10024; G06V 10/267; G06V 10/28; G06V 10/507; G06V 10/60; G06V 10/764; G06V 10/7715; G06V 2201/034
See application file for complete search history.

(56) References Cited

U.S. PATENT DOCUMENTS

| | | | |
|---|---|---|---|
| 12,036,059 B2* | 7/2024 | Itou | A61B 6/5217 |
| 2004/0010192 A1* | 1/2004 | Benaron | A61B 5/0075 600/431 |
| 2005/0276475 A1* | 12/2005 | Sawada | G06T 5/70 348/E3.018 |
| 2007/0058862 A1* | 3/2007 | Meier | G06T 5/40 382/104 |
| 2010/0056928 A1* | 3/2010 | Zuzak | G01J 3/2823 356/302 |
| 2011/0006220 A1* | 1/2011 | Kishima | G06T 7/0012 250/459.1 |
| 2016/0324420 A1* | 11/2016 | Zhu | A61B 6/00 |
| 2017/0055822 A1* | 3/2017 | Dana | A61B 5/1032 |
| 2017/0237958 A1* | 8/2017 | Themelis | G02B 21/008 348/34 |
| 2018/0225820 A1* | 8/2018 | Liang | G06V 10/82 |
| 2019/0008387 A1* | 1/2019 | Godavarty | A61B 5/7435 |
| 2019/0046041 A1* | 2/2019 | Kishima | G06T 7/30 |
| 2019/0231249 A1* | 8/2019 | Dascalu | A61B 5/7264 |
| 2019/0247126 A1* | 8/2019 | Ikehara | A61B 1/043 |
| 2020/0237445 A1* | 7/2020 | Snyder | A61B 34/30 |

FOREIGN PATENT DOCUMENTS

| | | | |
|---|---|---|---|
| JP | 2020156860 A | * | 10/2020 |
| WO | 2021165471 A1 | | 8/2021 |

OTHER PUBLICATIONS

Wikipedia, "Fluorescence imaging", downloaded Dec. 3, 2019 from Wikipedia.com, pp. 1-6.
Notification of Reasons for Refusal dispatched Nov. 26, 2024 for JP Application No. 2022-549882, a counterpart application of U.S. Appl. No. 17/801,218, 8 pgs.

\* cited by examiner

ASSISTING MEDICAL PROCEDURES WITH LUMINESCENCE IMAGES PROCESSED IN LIMITED INFORMATIVE REGIONS IDENTIFIED IN CORRESPONDING AUXILIARY IMAGES

This application claims priority to International Patent Application No. PCT/EP2021/054162 filed on Feb. 19, 2021, which claims priority to European Patent Application No. 20158847.2 filed on Feb. 21, 2020, which applications are incorporated by reference herein.

Technical Field

The present disclosure relates to imaging applications. More specifically, this disclosure relates to luminescence imaging for assisting medical procedures.

Background Art

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

Luminescence imaging, and especially fluorescence imaging, is a specific imaging technique that is used to acquire images providing a visual representation of objects, even if they are not visible directly. Luminescence imaging is based on a luminescence phenomenon, consisting of the emission of light by luminescence substances when subject to any excitation different from heating; particularly, a fluorescence phenomenon occurs in fluorescence substances (called fluorophores), which emit (fluorescence) light when they are illuminated.

Imaging techniques are commonly exploited in medical equipment to inspect (inner) body-parts of patients for assisting medical procedures thereon. For example, in Fluorescence Guided Surgery (FGS), also called Fluorescence Guided Resection (FGR) when relating to tumors, fluorescence agents (possibly adapted to reaching specific molecules of desired target bodies, such as tumors, and then to remaining immobilized thereon) are administered to the patients; the visualization of the fluorescence agents in corresponding fluorescence images, generally overlaid on corresponding reflectance images, facilitates operation of surgeons, for example, the recognition of tumors to be resected.

However, a field of view that is imagined often comprises, in addition to an actual region of interest, several foreign objects that are not of interest. For example, in (fluorescence) guided surgery this may be due to the presence, in addition to a surgical cavity, of surgical instruments, hands, surgical tools, surrounding body-parts (for example, skin around the surgical cavity or irrelevant organs within it) and background materials. The foreign objects generate spurious light, in addition to the fluorescence light actually of interest that is emitted by the fluorescence agent accumulated in a target body of the medical procedure (the tumor in the example at issue). Particularly, the spurious light may increase the fluorescence light. For example, this may be due to scattering and absorption phenomena; moreover, this may be due to the fluorescence agent that accumulates in surrounding body-parts (especially skin) as well because of (undesired) affinity with them. Conversely, the spurious light may reduce the fluorescence light unusually or artificially.

The spurious light (beyond being non-informative) is detrimental to the imaging of the tumor (or of any other target body). Particularly, the spurious light significantly biases the statistical distribution of (fluorescence) values of the fluorescence image; this adversely affects a next processing of the fluorescence image. For example, the fluorescence values are generally converted from a (fluorescence) range given by a measurement of the fluorescence light to a (display) range given by a display dynamics of a monitor used to display the fluorescence images. Therefore, the biasing of the statistical distribution of the fluorescence values by the spurious light (when increasing the fluorescence light) limits an extent of the fluorescence values that are used to display the region of interest. This makes the representation of the tumor therein less conspicuous. Moreover, the fluorescence image is often thresholded to discriminate the tumor from the rest of the fluorescence image according to a comparison of its fluorescence values with a threshold value; the threshold value is calculated automatically according to the fluorescence values. In this case as well, the biasing of the statistical distribution of the fluorescence values by the spurious light (either increasing or reducing the fluorescence light) affects the threshold value. This involves the risk of misclassifying the fluorescence values. As a result, it is possible to have over-detection of the tumor (false positive) and, especially, under-detection of the tumor (false negative); moreover, this hinders the detection of tumor foci. All of the above may have serious consequences for a health of the patient (such as an incomplete resection of the tumor).

A contribution of the spurious light is difficult (if not impossible) to remove from the fluorescence light of interest. Indeed, statistical techniques are quite ineffective for this purpose, since the spurious light is not easily distinguishable statistically. Optical filtering is quite ineffective as well, especially when the spurious light has the same spectral characteristics of the fluorescence light of interest (such as in case of the fluorescence agent accumulated in the skin). Moreover, manual adjustments of operative parameters of the medical equipment to limit the effects of the spurious light (including, for example, covering the foreign objects with non-fluorescent material) add further work (potentially requiring a dedicated operator needing specific training) and it is not reproducible; in any case, interaction with the medical equipment may be difficult, especially during surgical procedures because of sterility concerns.

WO-A-2013/096766 discloses a technique for imaging lesions in diagnostic applications. Mole borders are located in a visible light image. The visible light image and a fluorescent light image are aligned using locator fiducials on both of them. Mole features are extracted from one or both images.

WO-A-2019/232473 discloses a technique for automatically detecting and characterizing micro-objects, such as cells or beads located within a microfluidic device. Pixel data in an illuminated image are processed using a neural network to detect the micro-objects. A signal located within the corresponding boundary of each detected micro-object in non-illuminated images, such as fluorescent images, is used to measure characteristics of the micro-objects.

WO-A-2017/098010 discloses a technique for distinguishing live-beads from blank-beads in DNA/RNA-sequencing. The position of the beads is determined in a white-light illuminated image. The beads in their positions so determined are classified according to emission of electromagnetic radiation by fluorescent compounds.

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of processing a luminescence image limited to an informative region identified in an auxiliary image.

Particularly, an aspect provides a method for assisting a medical procedure. The method comprises acquiring a luminescence image (based on a luminescence light) and an auxiliary image (based on an auxiliary light different from this luminescence light) of a field of view; the field of view contains a region of interest comprising a target body of the medical procedure (containing a luminescence substance) and one or more foreign objects. An auxiliary informative region representative of the region of interest without the foreign objects is identified in the auxiliary image according to its content, and a luminescence informative region is identified in the luminescence image according to the auxiliary informative region. The luminescence image is processed limited to the luminescence informative region for facilitating an identification of a representation of the target body therein.

A further aspect provides a computer program for implementing the method.

A further aspect provides a corresponding computer program product.

A further aspect provides a computing device for performing the method.

A further aspect provides an imaging system comprising this computing device.

A further aspect provides a corresponding medical procedure.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis *mutandis* to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). Particularly.

DETAILED DESCRIPTION

Figure 1:
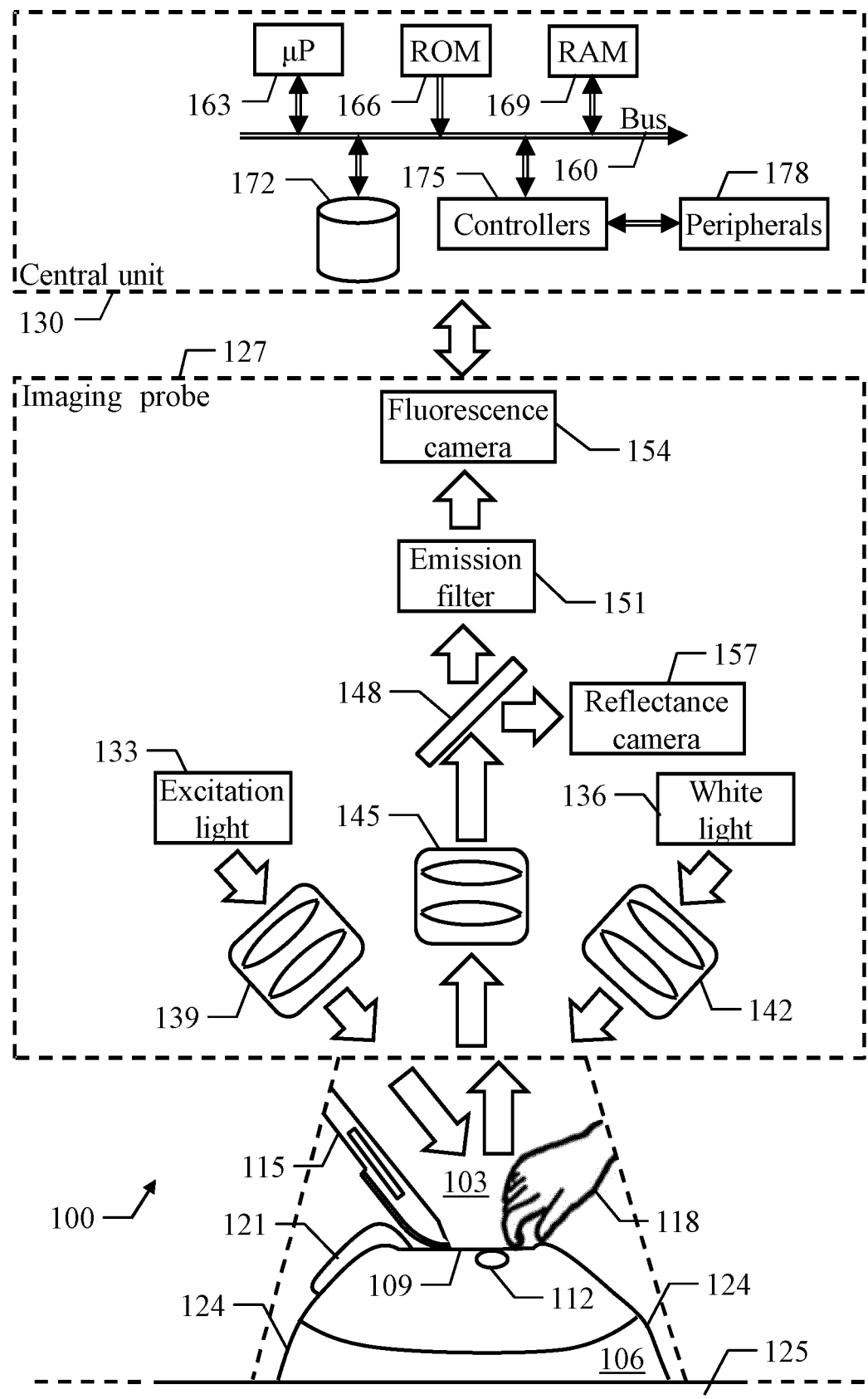
FIG. 1 shows a schematic block diagram of an imaging system that may be used to practice the solution according to an embodiment of the present disclosure.

With reference in particular to FIG. 1, a schematic block diagram is shown of an imaging system 100 that may be used to practice the solution according to an embodiment of the present disclosure.

The imaging system 100 allows imaging a corresponding field of view 103 (defined by a part of the world within a solid angle to which the imaging system 100 is sensitive). Particularly, the imaging system 100 is used in surgical applications (FGS and especially FGR) to assist a surgeon. In this specific case, the field of view 103 relates to a patient 106 undergoing a surgical procedure, to whom a fluorescence agent has been administered (for example, adapted to accumulating in tumors). The field of view 103 contains a surgical cavity 109 (for example, a small skin incision in minimally invasive surgery), which has been opened in the patient 106 to expose a corresponding body-part to be subject to the surgical procedure. Particularly, the body-part exposed in the surgical cavity 109 comprises a target body, or more, on which the surgeon has to act, for example, a tumor 112 to be resected. The field of view 103 generally contains one or more foreign objects (different from the surgical cavity 109); for example, these foreign objects may comprise one or more surgical instruments 115 (such as a scalpel), one or more hands 118 (such as of the surgeon), one or more surgical tools 121 (such as a gauze), one or more surrounding body-parts 124 (such as skin around the surgical cavity 109) and/or one or more background materials 125 (such as an operating table).

The imaging system 100 has an imaging probe 127 for acquiring images of the field of view 103 and a central unit 130 for controlling its operation.

Starting from the imaging probe 127, it has an illumination unit (for illuminating the field of view 103) and an acquisition unit (for acquiring images of the field of view 103) that comprise the following components. In the illumination unit, an excitation light source 133 and a white light source 136 generate an excitation light and a white light, respectively. The excitation light has wavelength and energy suitable to excite the fluorophores of the fluorescence agent (such as of Near Infra-Red, or NIR, type), whereas the white light appears substantially colorless to the human eye (such as containing all the wavelengths of the spectrum that is visible to the human eye at equal intensity). Corresponding delivery optics 139 and delivery optics 142 deliver the excitation light and the white light, respectively, to the (same) field of view 103. In the acquisition unit, collection optics 145 collect light from the field of view 103 (in an epi-illumination geometry). The collected light comprises fluorescence light that is emitted by any fluorophores present in the field of view (illuminated by the excitation light). Indeed, the fluorophores pass to an excited (electronic) state when they absorb the excitation light; the excited state is unstable, so that the fluorophores very shortly decay therefrom to a ground (electronic) state, thereby emitting the fluorescence light (at a characteristic wavelength, longer than the one of the excitation light because of energy dissipated as heat in the excited state) with an intensity depending on the amount of the fluorophores that are illuminated (and on other factors including fluorophores position within the field of view and the body-part). Moreover, the collected light comprises reflectance light (in the visible spectrum) that is reflected by any objects present in the field of view (illuminated by the white light). A beam-splitter 148 splits the collected light into two channels. For example, the beam-splitter 148 is a dichroic mirror transmitting and reflecting the collected light at wavelengths above and below, respectively, a threshold wavelength between a spectrum of the reflectance light and a spectrum of the fluorescence light (or vice-versa). In the (transmitted) channel of the beam-splitter 148 with the fluorescence light defined by the portion of the collected light in its spectrum, an emission filter 151 filters the fluorescence light to remove any excitation/white lights (which might be reflected by the field of view) and ambient lights (which might be generated by intrinsic fluorescence). A fluorescence camera 154 (for example, of EMCCD type) receives the fluorescence light from the emission filter 151 and generates a corresponding fluorescence (digital) image representing the distribution of the fluorophores in the field of view 103. In the other (reflected) channel of the beam-splitter 148 with the reflectance light defined by the portion of the collected light in its spectrum, a reflectance, or photograph, camera 157 (for example, of CCD type) receives the reflectance light and generates a corresponding reflectance (digital) image representing what is visible in the field of view 103.

Moving to the central unit 130, it comprises several units that are connected among them through a bus structure 160. Particularly, one or more microprocessors (μP) 163 provide a logic capability of the central unit 130. A non-volatile memory (ROM) 166 stores basic code for a bootstrap of the central unit 130 and a volatile memory (RAM) 169 is used as a working memory by the microprocessors 163. The central unit 130 is provided with a mass-memory 172 for storing programs and data (for example, a Solid-State-Disk, or SSD). Moreover, the central unit 130 comprises a number of controllers 175 for peripherals, or Input/Output (I/O) units. Particularly, the controllers 175 control the excitation light source 133, the white light source 136, the fluorescence camera 154 and the reflectance camera 157 of the imaging probe 127; moreover, the controllers 175 control further peripherals, denoted as a whole with the reference 178, such as one or more monitors for displaying images, a keyboard for entering commands, a trackball for moving a pointer on the monitor(s), a drive for reading/writing removable storage units (such as USB keys) and a network interface card (NIC) for connecting to a communication network (such as a LAN).

With reference now to FIG. 2A-FIG. 2E, different examples are shown of application of the solution according to an embodiment of the present disclosure.

Figure 2A:
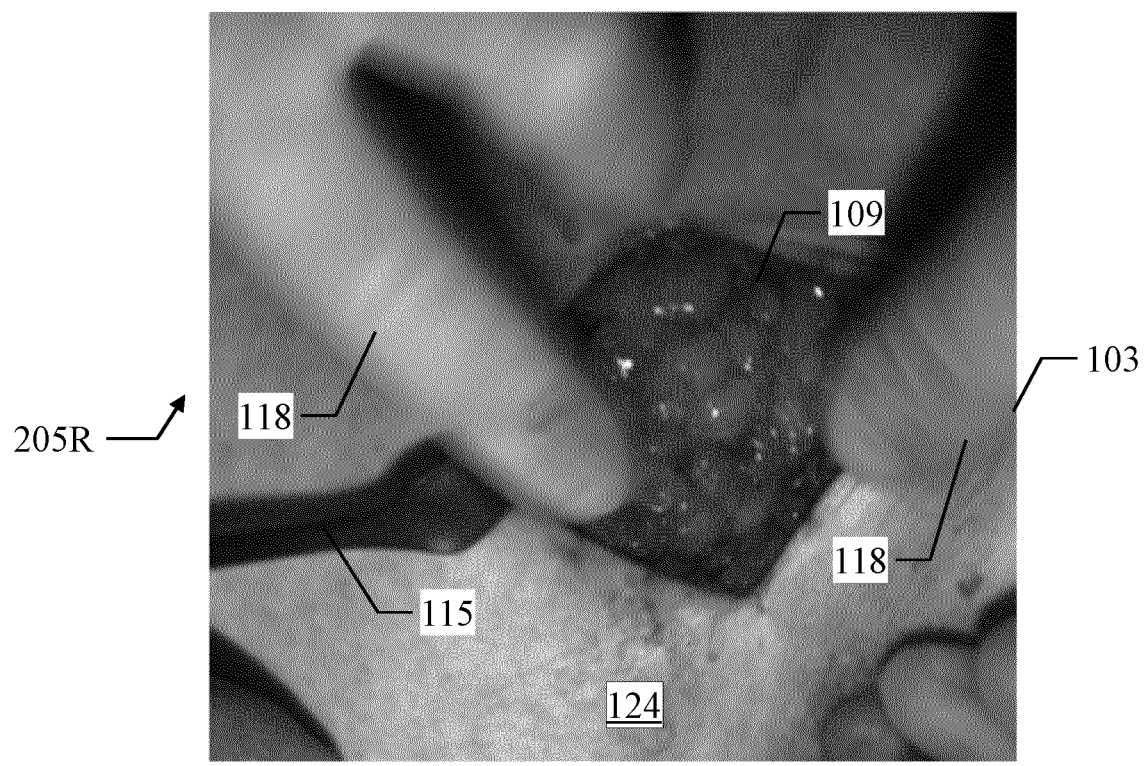
FIG. 2A-FIG. 2E show different examples of application of the solution according to an embodiment of the present disclosure.
Figure 2A:
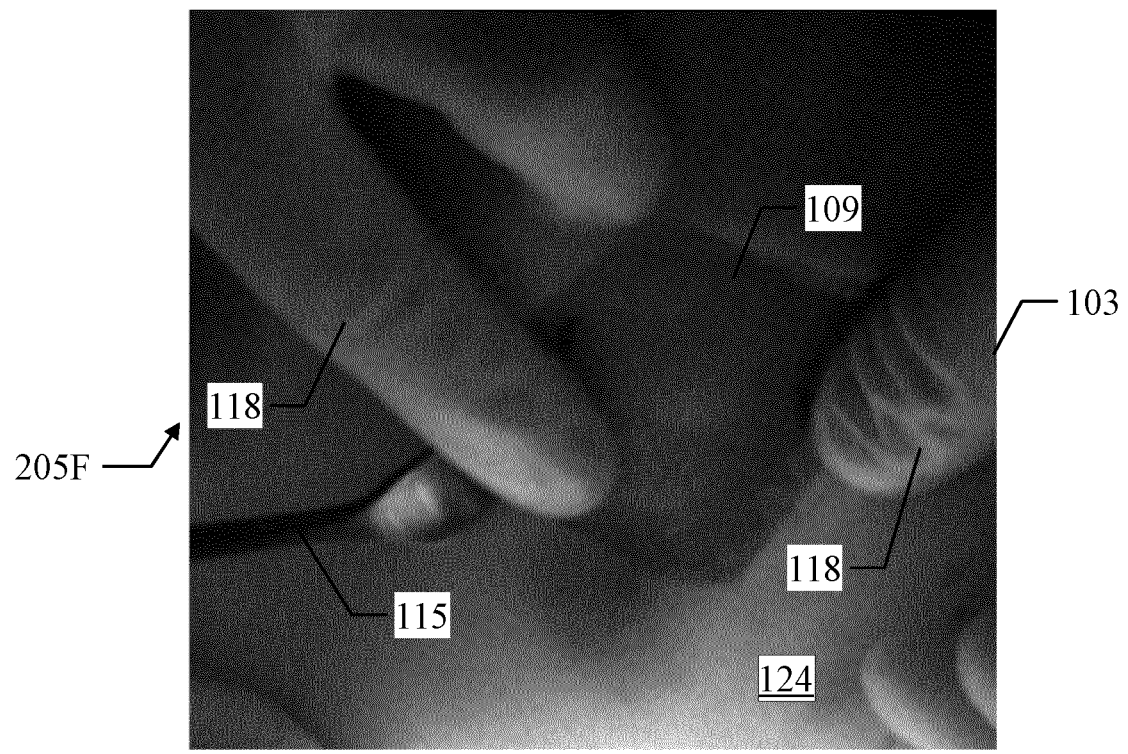

Starting from FIG. 2A, a pair of corresponding reflectance image 205R and fluorescence image 205F are shown. The reflectance image 205R and the fluorescence image 205F provide a concurrent representation (in terms of reflectance light and fluorescence light, respectively) of a same field of view 103. Particularly, the field of view 103 contains the surgical cavity 109 and some foreign objects, consisting of a surgical instrument 115, two surgeon hands 118 and surrounding skin 124 in the example at issue; the foreign objects 115-124 may be either arranged around the surgical cavity 109 (as in the case of the surgical instrument 115, part of the surgeon hands 118 and the surrounding skin 124) or overlapping the surgical cavity 109 (as in the case of part of the surgeon hands 118).

Figure 2B:
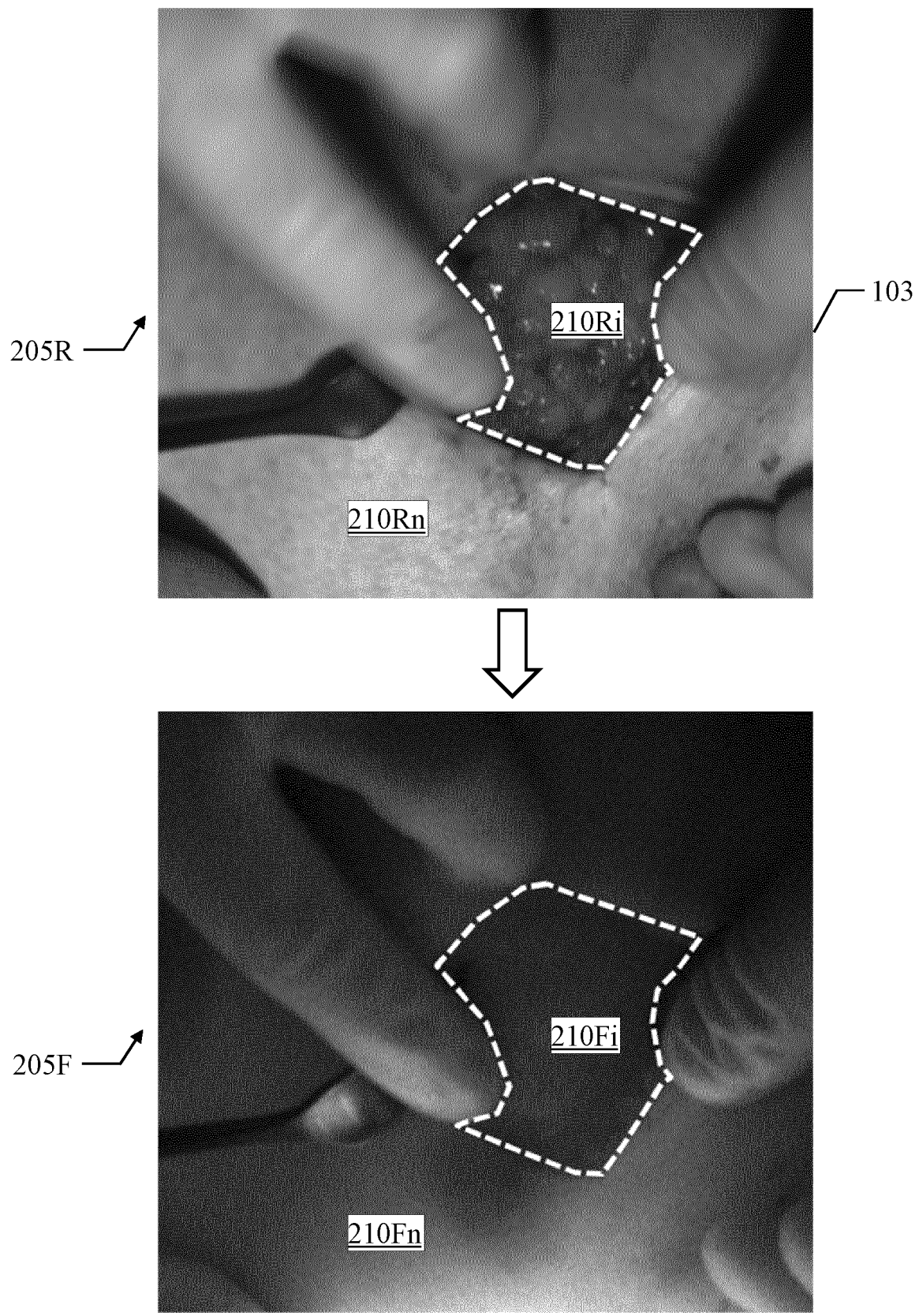

Moving to FIG. 2B, in the solution according to an embodiment of the present disclosure, a (reflectance) informative region 210Ri is identified in the reflectance image 205R according to its content. The informative region 210Ri represents the surgical cavity without the foreign objects (the surgical instrument, surgeon hands and surrounding skin in this case), and then an informative part of the field of view 103 that is actually of interest (i.e., a region of interest, or ROI, thereof). The rest of the reflectance image 205R then defines a (reflectance)non-informative region 210Rn that represents the foreign objects, and then a non-informative part of the field of view 103 that is not of interest. For example, as described in detail in the following, this result is achieved with semantic segmentation techniques (such as based on the use of a neural network).

The identification of the informative region 210Ri (and then of the non-informative region 210Rn as well) in the reflectance image 205R is transferred to the fluorescence image 205F. Particularly, a (fluorescence) informative region 210Fi is identified in the fluorescence image 205F corresponding to the informative region 210Ri. As a result, the rest of the fluorescence image 205F defines a (fluorescence) non-informative region 210Fn corresponding to the non-informative region 210Rn.

As described in detail in the following, a processed image is now generated by processing the fluorescence image 205F limited to its informative region 210Fi; the processing of the fluorescence image 205F is thus based on (fluorescence) values of the fluorescence image 205F only in the informative region, for example, on their distribution (such as range, probability). This processing of the fluorescence image 205F is aimed at facilitating the identification of a representation of the tumor therein (for example, by auto-scaling or thresholding the informative region 210Fi).

As a result, it is possible to take into account only the (informative) representation of the surgical cavity in the fluorescence image 205F, instead disregarding the (non-informative) representation of the foreign objects (around and/or overlapping it). This avoids (or at least substantially reduces) any adverse effect of the foreign objects in the imaging of the surgical cavity. Particularly, the statistical distribution of the fluorescence values on which the processing of the fluorescence image 205F is based is now unbiased (since the fluorescence values in the non-informative region 210Fn do not contribute thereto).

Figure 2C:
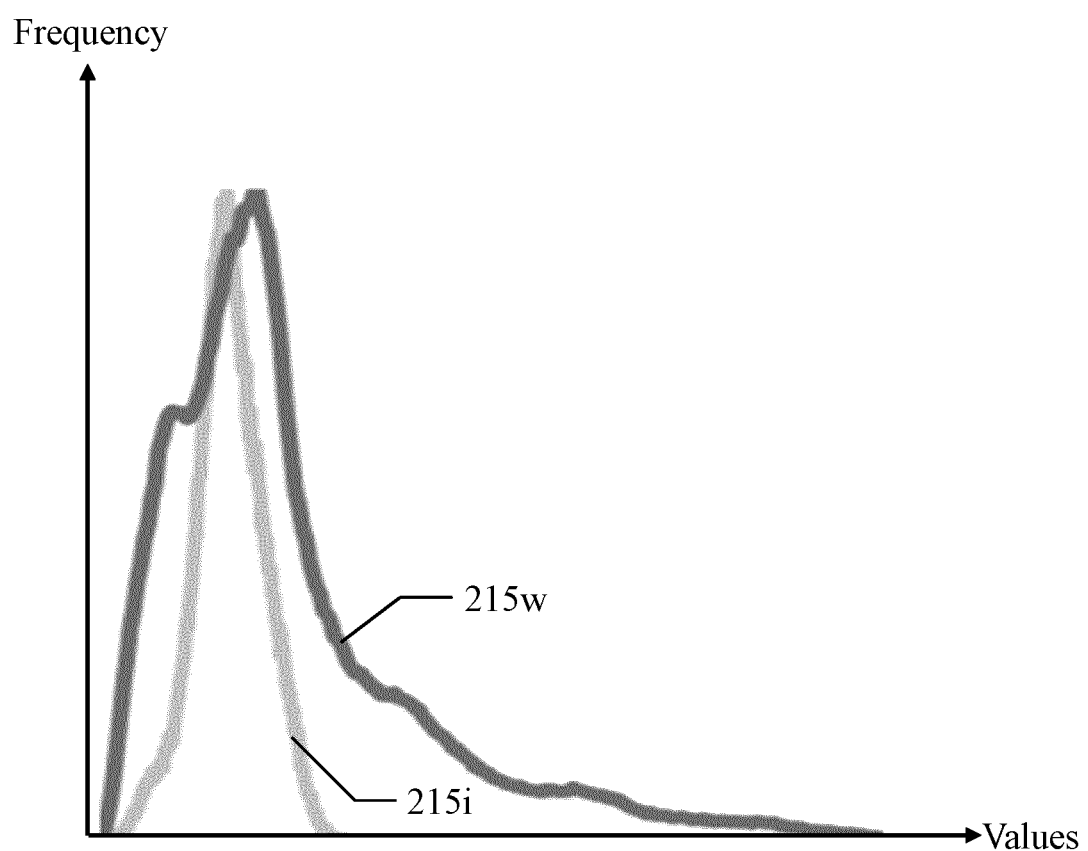

For example, FIG. 2C shows a curve 215w and a curve 215i representing corresponding probability functions of the fluorescence values in the whole fluorescence image and only in its informative region, respectively; the probability functions 215w,215i approximate corresponding histograms of the fluorescence values, in a qualitative diagram plotting the fluorescence values on the abscissa-axis and their frequency on the ordinate-axis. As can be seen, the probability function 215i is far narrower than the probability function 215w. Therefore, the processing of the fluorescence image limited to the informative region benefits from this narrower probability distribution of its fluorescence values.

Figure 2D:
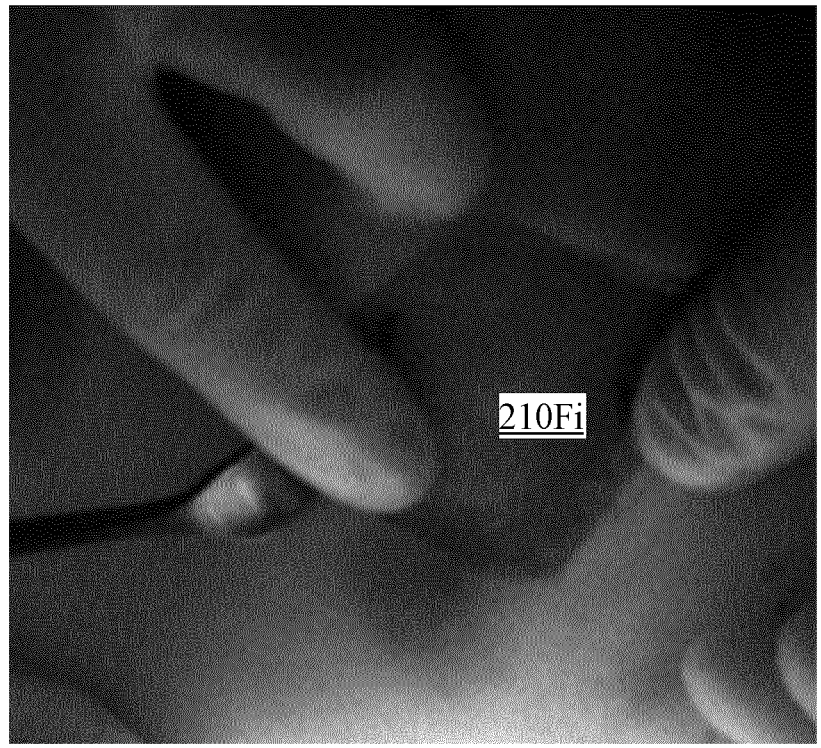
Figure 2D:
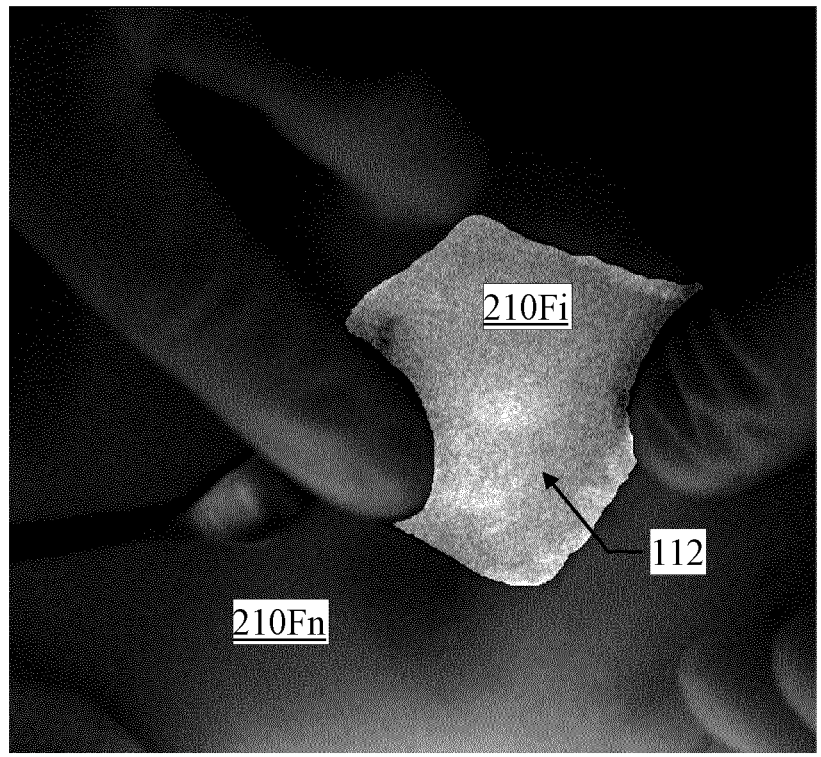

Particularly, FIG. 2D shows a processed image that has been generated by auto-scaling the whole fluorescence image, referred to as auto-scaled (fluorescence) image 220Fw. The auto-scaled image 220Fw has been obtained by applying a mapping function to all the fluorescence values of the fluorescence image for converting them from a (fluorescence) range given by a measurement resolution of the fluorescence light to a (display) range given by a display dynamics of a monitor used to display it (for example, based on a logarithmic law to obtain images with a well-balanced contrast). The figure also shows a processed image that has been generated by auto-scaling the fluorescence image limited to its informative region 210Fi (and further by auto-scaling the fluorescence image limited to its non-informative region 210Fn), referred to as auto-scaled (fluorescence) image 220Fi. Particularly, the auto-scaled image 220Fi has now been obtained by applying corresponding mapping functions to the fluorescence values in the informative region 210Fi and to the fluorescence values in the non-informative region 210Fn separately (with the fluorescence values in the non-informative region 210Fn that are reduced by a scaling factor to mask its content). In the auto-scaled image 220Fw, the wide statistical distribution of its fluorescence values limits an extent of the fluorescence values that are available within the display range for mapping the fluorescence values in the informative region 210Fi (because of their narrower statistical distribution). This reduces the differences among the fluorescence values in the informative region 210Fi, thereby making very difficult (if not impossible) to identify its portions with higher concentration of the fluorescence agent representing the tumor to be resected. In the auto-scaled image 220Fi, instead, the whole display range is available for mapping the fluorescence values in the informative region 210Fi. This increases the differences among the fluorescence values in the informative region 210Fi, thereby making the representation of the tumor 112 far more conspicuous.

Figure 2E:
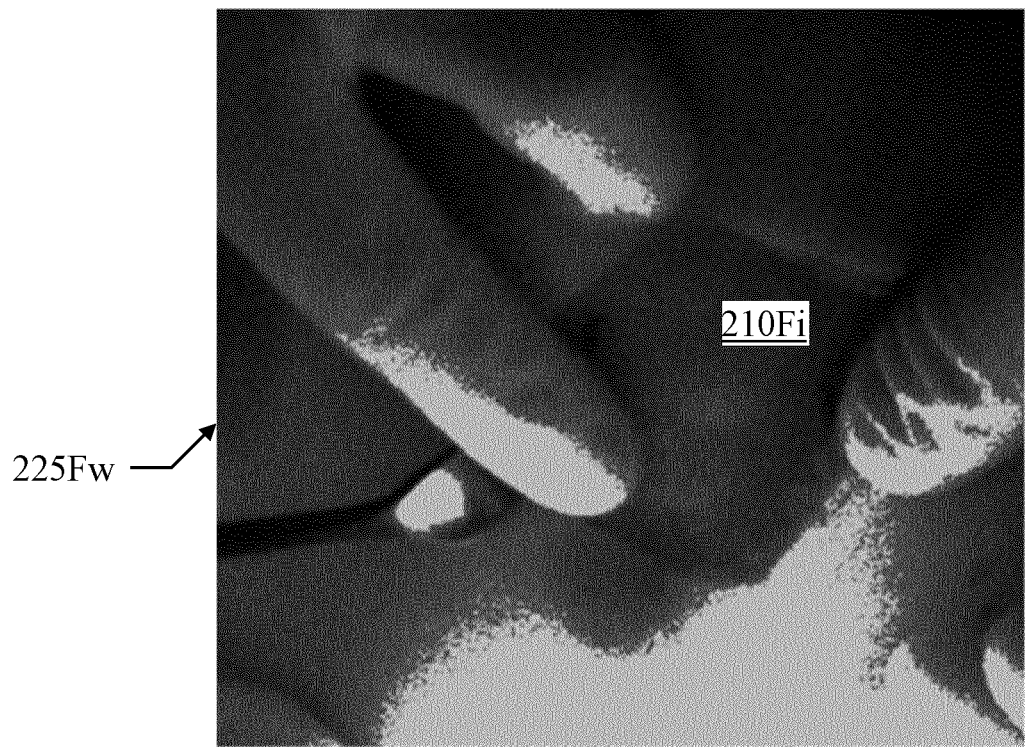
Figure 2E:
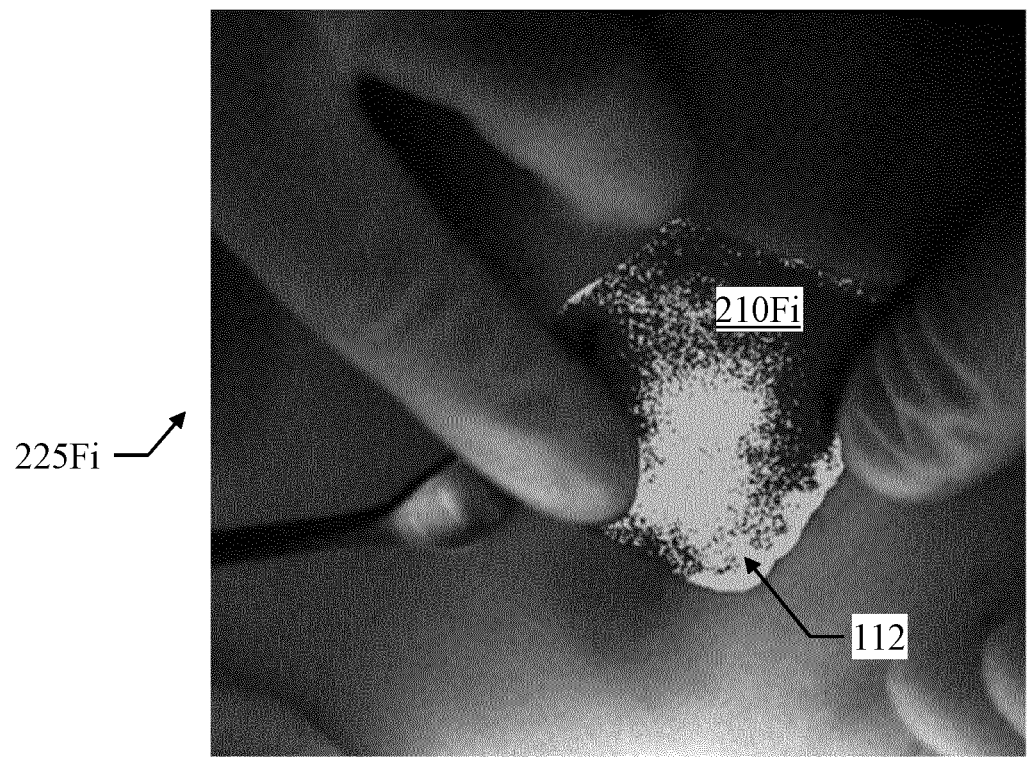

Moving to FIG. 2E, a different processed image is shown that has been generated by thresholding the whole fluorescence image, referred to as thresholded (fluorescence) image 225Fw. Particularly, the thresholded image 225Fw has been obtained by partitioning the fluorescence image into a (foreground) target segment and a (background) non-target segment, whose fluorescence values are above and below, respectively, a threshold value calculated according to the fluorescence values (for example, minimizing an inter-class variance); the target segment representing the tumor is then highlighted (for example, in color) with respect to the non-target segment representing a rest of the surgical cavity different from the tumor (for example, in black-and-white). The figure also shows a processed image that has been generated in the same way by thresholding the informative region 210Fi only, referred to as thresholded (fluorescence) image 225Fi. In the thresholded image 230Fw, the wide statistical distribution of its fluorescence values rises the threshold value (because of its higher fluorescence values). This causes the classification of the fluorescence values in the informative region 210Fi to the non-target segment, thereby making the tumor disappear. In the thresholded image 225Fi, instead, the fluorescence values in the informative region 210Fi are classified correctly, thanks to the lower threshold value (because of their narrower statistical distribution). This allows discriminating the tumor 112 within the informative region 210Fi.

The above-described solution facilitates the identification of the tumor (or any other target body). For example, the risk of over-detection of the tumor (false positive) and, especially, of under-detection of the tumor (false negative) is significantly reduced. This avoids (or at least significantly reduces) excessive removal of healthy tissues and, especially, incomplete resection of the tumor; moreover, this significantly improves the detection of tumor foci. All of the above has a beneficial effect on the health of the patient.

Figure 3:
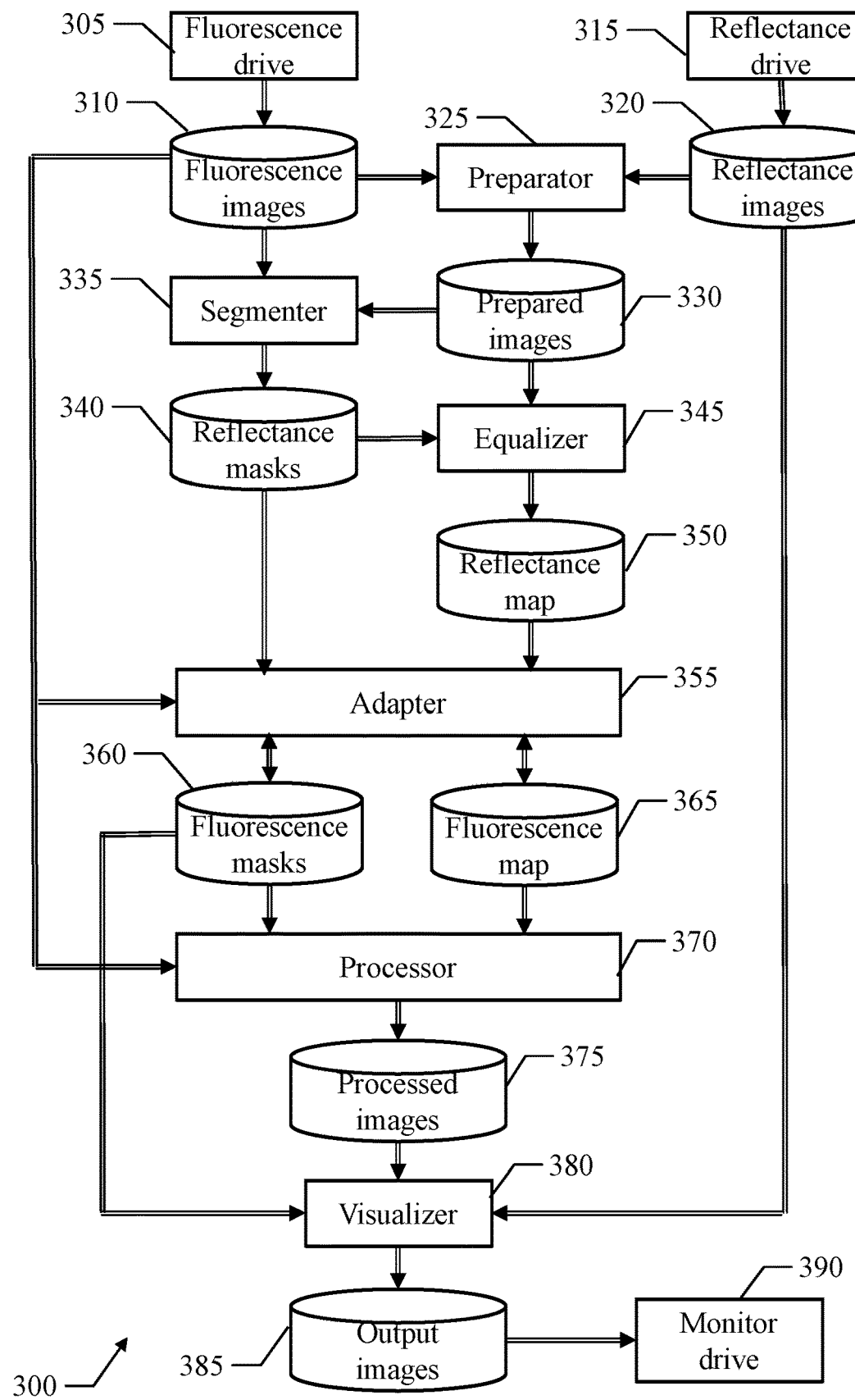
FIG. 3 shows the main software components that may be used to implement the solution according to an embodiment of the present disclosure.

With reference now to FIG. 3, the main software components are shown that may be used to implement the solution according to an embodiment of the present disclosure.

All the software components (programs and data) are denoted as a whole with the reference 300. The software components 300 are typically stored in the mass memory and loaded (at least in part) into the working memory of the central unit of the imaging system when the programs are running, together with an operating system and other application programs not directly relevant to the solution of the present disclosure (thus omitted in the figure for the sake of simplicity). The programs are initially installed into the mass memory, for example, from removable storage units or from the communication network. In this respect, each program may be a module, segment or portion of code, which comprises one or more executable instructions for implementing the specified logical function.

A fluorescence drive 305 drives a fluorescence unit of the imaging system (comprising the excitation light source and the fluorescence camera) dedicated to acquiring the fluorescence images of the field of view suitable illuminated for this purpose. The fluorescence drive 305 accesses (in write mode) a fluorescence images repository 310, which stores a sequence of fluorescence images being acquired in succession during an imaging process that is in progress (to assist a corresponding surgical procedure). Each fluorescence image is defined by a bitmap comprising a matrix of cells (for example, with 512 rows and 512 columns) each storing the (fluorescence) value of a pixel, i.e., a basic picture element corresponding to a (fluorescence) location of the field of view; each pixel value defines the brightness of the pixel as a function of an intensity of the fluorescence light emitted by the location, and then of an amount of the fluorescence agent present therein (for example, from black when no fluorescence agent is present to white as the amount of the fluorescence agent increases). Likewise, a reflectance drive 315 drives a reflectance unit of the imaging system (comprising the white light source and the reflectance camera) dedicated to acquiring the reflectance images of the field of view suitable illuminated for this purpose. The reflectance drive 315 accesses (in write mode) a reflectance images repository 320, which stores a sequence of reflectance images being acquired in succession during the same imaging process (synchronized with the fluorescence images in the corresponding repository 310). Each reflectance image is defined by a bitmap comprising a matrix of cells (with either the same or different size with respect to the reflectance images) each storing the (reflectance) value of a pixel corresponding to a (reflectance) location of the field of view (either the same or different with respect to the fluorescence locations); each pixel value defines the visible light that is reflected by the location (such as its RGB components). A preparator 325 optionally pre-processes the reflectance images for preparing them to the next identification of the informative region therein. The preparator 325 accesses (in read mode) the reflectance images repository 320 and (optionally) the fluorescence images repository 310, and it accesses (in write mode) a prepared reflectance images repository 330. The prepared reflectance images repository 330 comprises an entry for each reflectance image in the corresponding repository 320; the entry stores a corresponding prepared reflectance image when the reflectance image is suitable for identifying the informative region or a null value otherwise. The prepared reflectance image is formed by a matrix of cells with either the same or different size with respect to the reflectance images, each storing a corresponding pixel (prepared) value. A segmenter 335 segments the prepared reflectance images (semantically) into their informative regions and non-informative regions; each prepared reflectance image is segmented according to the content thereof and possibly according to the content of the corresponding fluorescence image as well (which although semantically poorer may provide additional information being potentially useful). The segmenter 335 accesses (in read mode) the prepared reflectance images repository 330 and (optionally) the fluorescence images repository 310, and it accesses (in write mode) a reflectance segmentation masks repository 340. The reflectance segmentation masks repository 340 comprises an entry for each one in the prepared reflectance images repository 330; the entry stores a corresponding reflectance segmentation mask for a prepared reflectance image or a null value otherwise. The reflectance segmentation mask is formed by a matrix of cells with the same size as the prepared reflectance images, each storing a label indicating a classification of the corresponding pixel; in this case with only two classes (informative class and non-informative class for the informative region and the non-informative region, respectively), the label is a binary value, for example, which is asserted (such as at the logic value 1) when the pixel belongs to the informative region and it is deasserted (such as at the logic value 0) when the pixel belongs to the non-informative region. An equalizer 345 determines optical properties relating to the fluorescence light of the material represented in the prepared reflectance images limited to their informative regions. The equalizer 345 accesses (in read mode) the prepared reflectance images repository 330 and the reflectance segmentation masks repository 340, and it accesses (in write mode) a reflectance equalization maps repository 350. The reflectance equalization maps repository 350 comprises an entry for each one in the prepared reflectance images repository 330; the entry stores a corresponding reflectance equalization map for a prepared reflectance image or a null value otherwise. The reflectance equalization map is formed by a matrix of cells with the same size as the prepared reflectance images, each storing an (optical) value of an optical parameter (or more) relating to the fluorescence light of the material represented in the corresponding pixel (for example, its reflectance, absorption and so on). An adapter 355 optionally adapts the reflectance segmentation masks and the reflectance equalization maps to the fluorescence images, so as to equalize their sizes and to synchronize them. The adapter 355 accesses (in read mode) the reflectance segmentation masks repository 340, the reflectance equalization maps repository 350 and the fluorescence images repository 310, and it accesses (in read/write mode) a fluorescence segmentation masks repository 360 and a fluorescence equalization maps repository 365. The fluorescence segmentation masks repository 360 comprises a fluorescence segmentation mask for each fluorescence image in the corresponding repository 310. The fluorescence segmentation mask is formed by a matrix of cells with the same size as the fluorescence images, each storing the label of the corresponding pixel as above (i.e., asserted or deasserted when the pixel belongs to the informative region or to the non-informative region, respectively). The fluorescence equalization maps repository 365 comprises a fluorescence equalization map for each fluorescence image in the corresponding repository 310. The fluorescence equalization map is formed by a matrix of cells with the same size as the fluorescence images, each storing the optical value of the corresponding pixel.

A processor 370 (post-)processes the fluorescence images limited to their informative regions for facilitating the identification of the representation of the tumor therein (for example, by auto-scaling and/or thresholding them). The processor 370 accesses (in read mode) the fluorescence images repository 310, the fluorescence segmentation masks repository 360 and the fluorescence equalization maps repository 365, and it accesses (in write mode) a processed fluorescence images repository 375. The processed fluorescence images repository 375 comprises a processed fluorescence image for each fluorescence image in the corresponding repositories 310; for example, the processed fluorescence image is an auto-scaled fluorescence image (in case of auto-scaling) or a thresholded fluorescence image (in case of thresholding). The processed fluorescence image is formed by a matrix of cells with the same size as the fluorescence images, each storing a corresponding pixel (processed, i.e., auto-scaled/thresholded) value. A visualizer 380 generates output images based on the processed fluorescence images for their visualization. The visualizer 380 accesses (in read mode) the processed fluorescence images repository 375 and (optionally) the fluorescence masks repository 360 and the reflectance images repository 320, and it accesses (in write mode) an output images repository 385. The output images repository 385 comprises an output image for each processed fluorescence image in the corresponding repository 375. For example, the output image is equal to the processed fluorescence image alone, or to the processed fluorescence image overlaid on the corresponding reflectance image. A monitor drive 390 drives the monitor of the imaging system to display the output images (substantially in real-time during the surgical procedure). The monitor drive 390 accesses (in read mode) the output images repository 385.

Figure 4A:
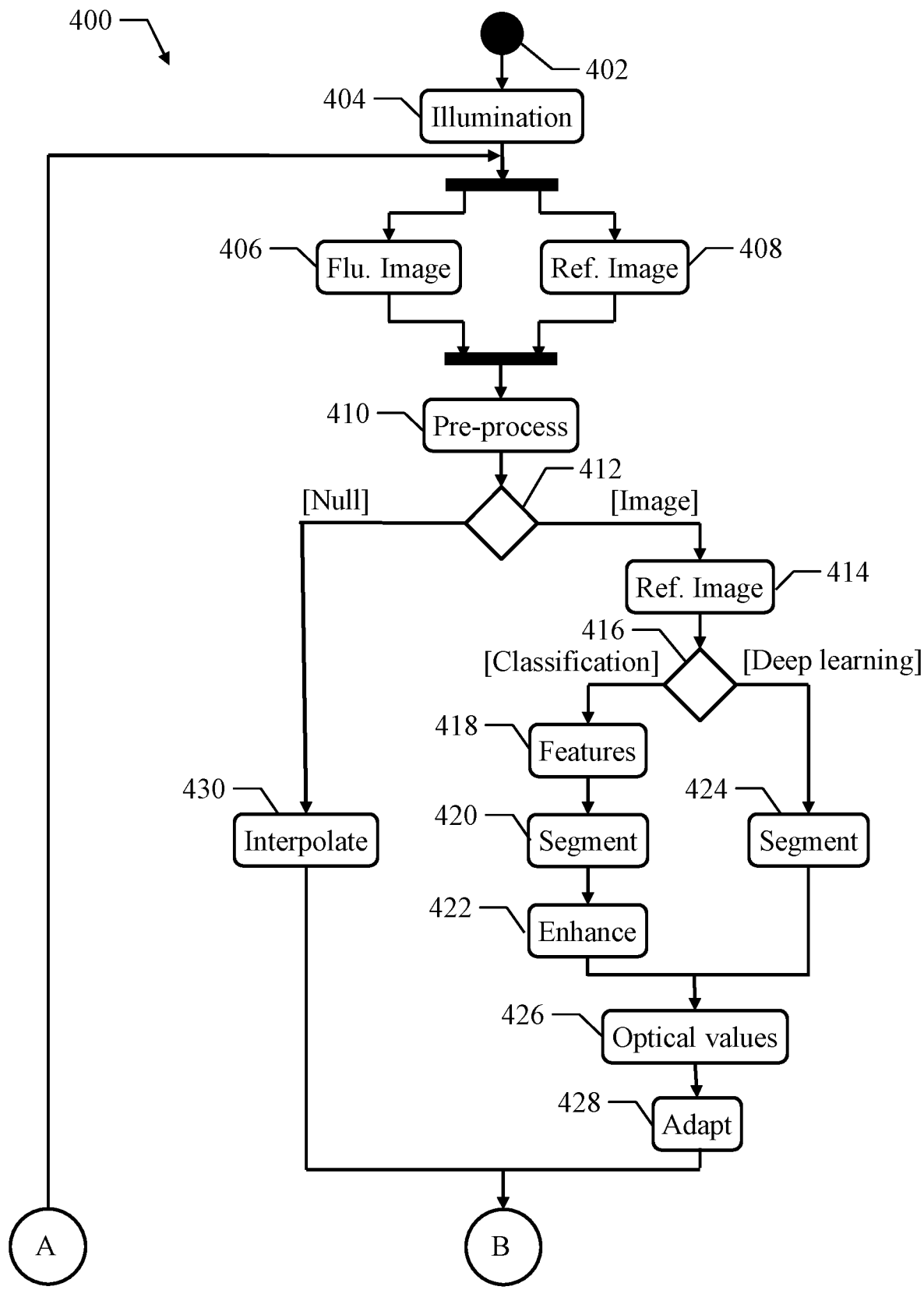
FIG. 4A-FIG. 4B and FIG. 5 show different activity diagrams describing the flow of activities relating to an implementation of the solution according to an embodiment of the present disclosure.
Figure 4B:
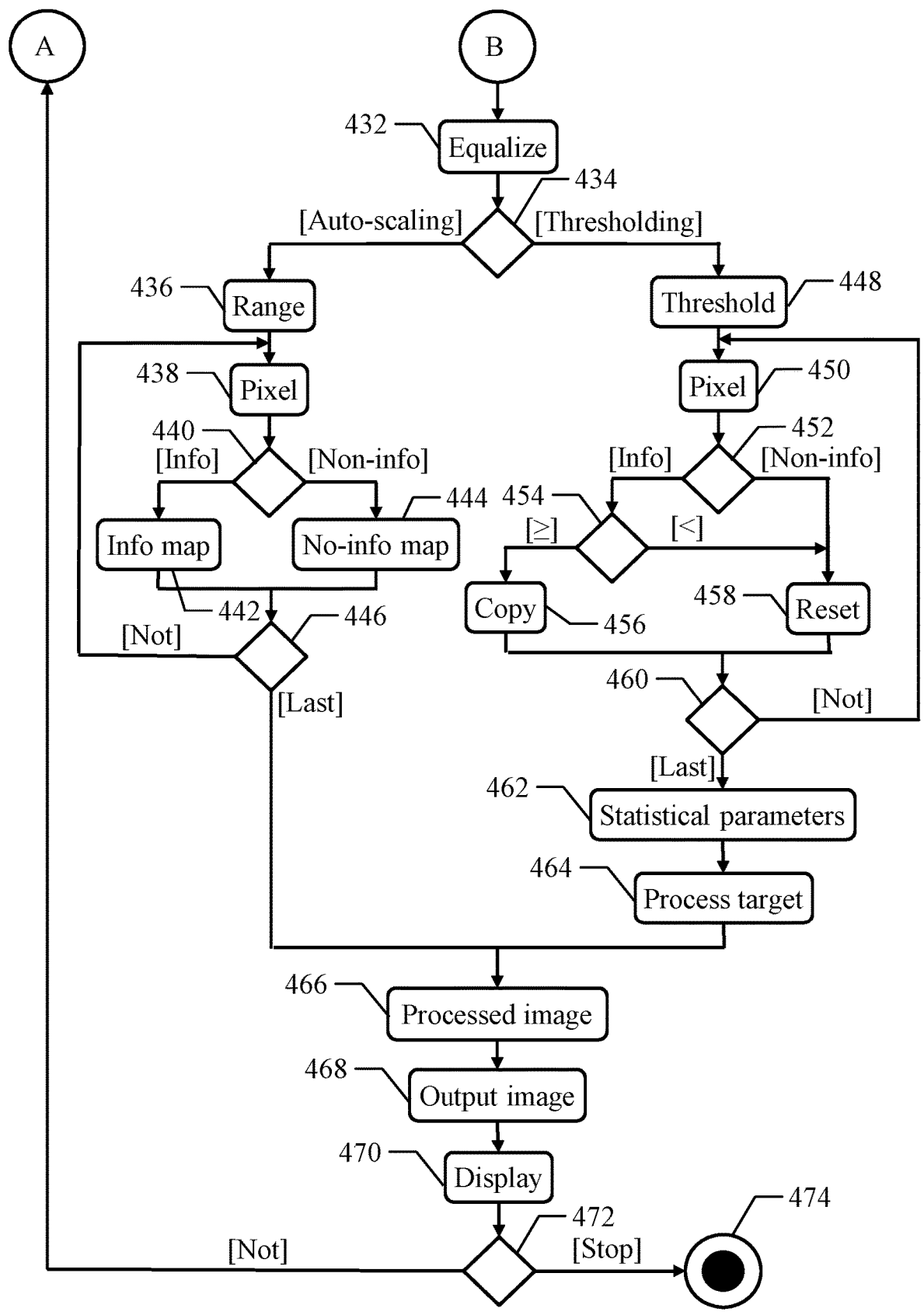
Figure 5:
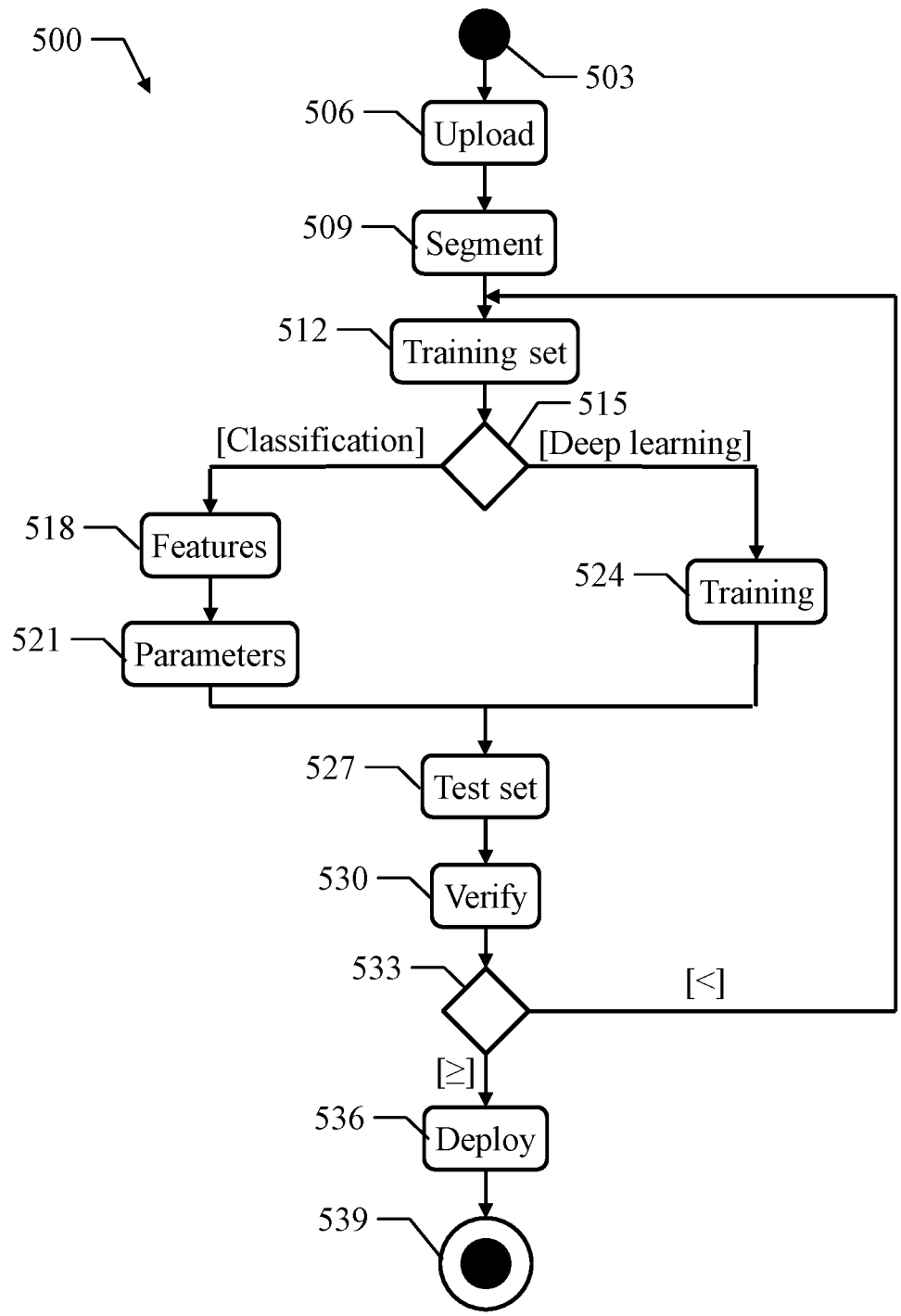

With reference now to FIG. 4A-FIG. 4B and FIG. 5, different activity diagrams are shown describing the flow of activities relating to an implementation of the solution according to an embodiment of the present disclosure. In this respect, each block may correspond to one or more executable instructions for implementing the specified logical function on a corresponding computing device.

Starting from FIG. 4A-FIG. 4B, their activity diagram represents an exemplary process that may be used to imaging a patient with a method 400. The process is executed on the central unit of the imaging system during a surgical procedure on the patient. The solution according to an embodiment of the present disclosure (wherein the identification of the informative region in the reflectance images is transferred to the corresponding fluorescence images for facilitating the identification of the tumor therein) may be applied indiscriminately (always) or selectively (for example, by activating/deactivating it in response to a corresponding command, such as entered by pressing a dedicated button of the imaging system).

Before the surgical procedure (even few days before it), a health care operator (for example, a nurse) administers a fluorescence agent to the patient. The fluorescence agent (for example, Indocyanine Green, Methylene Blue and so on) is suitable to reach a specific (biological) target body, such as a tumor to be resected. This result may be achieved by using either a non-targeted fluorescence agent (adapted to accumulating in the target body without any specific interaction therewith, such as by passive accumulation) or a targeted fluorescence agent (adapted to attaching to the target body by means of a specific interaction therewith, such as achieved by incorporating a target-specific ligand into the formulation of the fluorescence agent, for example, based on chemical binding properties and/or physical structure adapted to interacting with different tissues, vascular properties, metabolic characteristics and so on). The fluorescence agent is administered to the patient intravenously as a bolus (with a syringe); as a consequence, the fluorescence agent circulates within the vascular system of the patient until reaching the tumor and binding thereto; the remaining (unbound) fluorescence agent is instead cleared from the blood pool (according to a corresponding half-life time). After a waiting time allowing the fluorescence agent to accumulate in the tumor and to wash-out from the other body-parts of the patient (for example, from some minutes to 24-72 hours), the surgical procedure may start. At this point, the operator places the imaging probe close to a region of the patient wherein a surgical cavity is opened by a surgeon; the operator then enters a start command into the imaging system (for example, with its keyboard).

In response thereto, an imaging process begins by passing from the black start circle 402 to block 404. At this point, the fluorescence drive and the reflectance drive turn on the excitation light source and the white light source, respectively, for illuminating the field of view. The flow of activity then forks into two operations that are performed concurrently. Particularly, the fluorescence drive at block 406 acquires a (new) fluorescence image and adds it to the corresponding repository. At the same time, the reflectance drive at block 408 acquires a (new) reflectance image and adds it to the corresponding repository. In this way, the fluorescence image and the reflectance image are acquired substantially at the same time and they provide different representations (in terms of fluorescence light and visible light, respectively) of the same field of view that are spatially coherent (i.e., a predictable correlation exists among their pixels, down to a perfect identity).

The flow of activity joints again at block 410 from the block 406 and the block 408, wherein the preparator retrieves the reflectance image just added to the corresponding repository and optionally pre-processes it for preparation to the next identification of the informative region therein. For example, the preparator may verify whether the reflectance image is suitable for identifying the informative region. For this purpose, an average and/or a variance of its pixel values may be calculated. If the average is (possibly strictly) lower than a (darkness) threshold (meaning that the reflectance image is too dark) and/or if the variance is (possibly strictly) higher than a (blurry) threshold (meaning that the reflectance image is too blurry), a quality of the reflectance image is deemed not acceptable to provide a meaningful identification of the informative region; in this case, the preparator disregards the reflectance image by adding the null value to the prepared reflectance image repository. Conversely (meaning that the quality of the reflectance image is acceptable and then the identification of the informative region therein is feasible), the preparator may apply one or more filters to further improve the quality of the reflectance image (for example, normalizing colors, reducing noise, correcting illumination, reducing distortion, removing reflection and so on). Particularly, if the average is (possibly strictly) higher than the darkness threshold but lower than a higher (brightness) threshold (meaning that the reflectance image is not very bright), such as equal to 1.2-1.5 thereof, the preparator may apply a histogram equalization to the reflectance image (by spreading the most frequent pixel values to obtain a substantial flat histogram thereof); indeed, experimental results have shown that the histogram equalization improves performance in this case, whereas it may degrade performance otherwise. In addition or in alternative, the preparator may downscale the reflectance image to reduce computational complexity (for example, with low-pass filtering followed by sub-sampling). In addition or in alternative, the preparator may group the pixels of the reflectance image into substantially homogenous groups thereof, each one represented by a group value based on the corresponding pixel values, to simplify the identification of the informative region (for example, by applying clustering, graph-based, random walks, watershed edge detection and similar algorithms). In addition or in alternative, the preparator may apply a motion compensation algorithm (to align the reflectance image with the fluorescence image) and/or a warping algorithm (to correct a distortion of the reflectance image with respect to the fluorescence image). In any case, the preparator then adds the prepared reflectance image so obtained (possibly equal to the corresponding reflectance image) to the corresponding repository.

The flow of activity branches at block 412 according to the content of the entry just added to the prepared reflectance images repository. If the entry contains a (prepared) reflectance image, the segmenter at block 414 extracts this reflectance image from the corresponding repository for its semantic segmentation. In computer vision, semantic segmentation is a specific type of segmentation (generally aimed at partitioning an image into disjoint portions, or segments, with substantially homogenous characteristics), wherein the segments represent entities belonging to different classes having corresponding meanings (i.e., concepts abstracting common characteristics of multiple instances thereof). In this specific case, the semantic segmentation is aimed at partitioning the reflectance image into the informative region representing the surgical cavity without the foreign objects and the non-informative region representing the foreign objects (i.e., surgical instruments, hands, surgical tools, surrounding body-parts and/or background materials). The flow of activity then branches at block 416 according to an implementation of the segmenter. Particularly, when the segmenter is based on a classification algorithm the blocks 418-422 are executed, whereas when the segmenter is based on a deep learning technique the block 424 is executed.

With reference now to the block 418 (classification algorithm), the segmenter performs a feature extraction step for extracting one or more features from the reflectance image and possibly from the corresponding fluorescence image as well (pre-determined to be the best suited for this purpose, as described in the following); each feature is a (measurable) property that represents a distinctive characteristic of the reflectance/fluorescence image. Examples of these features are saturation, hue, brightness, Histogram of Oriented Gradient (HOG), variance, Bag Of Visterms (BOV), Scale-Invariant Feature Transform (SIFT) and so on. More specifically, the segmenter calculates one or more features maps; each feature map is formed by a matrix of cells with the same size as the reflectance/fluorescence image, each storing a (feature) value of a corresponding feature. For this purpose, the segment applies corresponding filters to the reflectance/fluorescence image (for example, smoothing, such as Gaussian blur, Kuwhara, anisotropic diffusion and the like, statistic, such as mean, median, entropy and the like, edge detector, such as Sobel, Prewitt, Canny and the like, derivatives, Hessian, Laplacian and so on); each filter calculates the feature value of each location according to the corresponding pixel value, possibly taking into account the pixel values of its neighbor pixels. The segmenter at block 420 calculates the reflectance segmentation mask corresponding to the reflectance image by applying a specific classification algorithm to the feature maps, and then adds it to the corresponding repository. For example, the classification algorithm is the Conditional Random Field (CRF) algorithm. Basically, the CRF algorithm calculates the label of each pixel by an inference step determining the value of the label that maximizes the posterior probability that the pixel belongs to the corresponding class. The posterior probability is based on a node (or unary) potential only depending on the feature values of the pixel and an edge (or pairwise) potential taking into account its neighbor pixels (either their labels to smooth transitions among segments or their feature values to model similarities). The segmenter at block 422 optionally enhances the reflectance segmentation mask so obtained. For example, the segmenter may perform a fill-hole step wherein any disconnected portions of the non-informative region, i.e., completely surrounded by the informative region, are assigned to the informative region (assuming that no foreign object may be completely surrounded by the surgical cavity). In addition or in alternative, the segmenter may perform one or more smoothing steps to remove isolated misclassified pixels (such as by applying erosion, dilation, box filter convolution and similar algorithms).

With reference instead to the block 424 (deep learning), the segmenter is an (artificial) neural network, for example, a U-Net (suitably trained for this purpose, as described in the following). Basically, deep learning is a specific type of machine learning (used to perform a specific task, in this case segmenting the reflectance image semantically, without using explicit instructions but inferring how to do so automatically from examples, which is based on neural networks. A neural network is a data processing system that approximates operation of human brain. The neural network comprises basic processing elements (neurons), which perform operations based on corresponding weights; the nodes are connected via unidirectional channels (synapses), which transfer data among them. The neurons are organized in layers performing different operations, always comprising an input layer and an output layer for receiving input data and for providing output data, respectively (in this case, the reflectance image with possibly the corresponding fluorescence image and the corresponding reflectance segmentation mask, respectively). A deep neural network (DNN) is a particular type of neural network with one or more (hidden) layers between the input layer and the output layer. A Convolutional Neural Network (CNN) is a particular type of deep neural network wherein one or more of its layers perform (cross) convolution operations. Particularly, the CNN comprises one or more convolutional layers that calculate corresponding feature maps followed by one or more pooling layers that reduce their resolution; one or more fully connected layers then segment the fluorescence image according to these (reduced) feature maps. A U-Net is a specific convolutional neural network, wherein a contracting path (formed by the convolutional layers and the pooling layers) is followed by an expanding path; conversely, the expanding path comprises one or more up-sampling layers increasing the resolution of the feature maps followed by one or more convolutional layers assembling them, without any fully connected layers (with the expanding path that is substantially symmetric to the contracting path thereby providing a U-shaped architecture). In this case, the segmenter (receiving the reflectance/fluorescence image) directly generates the reflectance segmentation mask and adds it to the corresponding repository.

In both cases, the flow of activity again merges at block 426 from the block 422 or the block 424. At this point, the equalizer retrieves the reflectance segmentation mask just added to its repository and the corresponding (prepared) reflectance image from its repository for determining the optical properties of the reflectance image limited to its informative region. For this purpose, the equalizer takes each pixel of the reflectance image into account; if the corresponding label in the reflectance segmentation mask is asserted (meaning that the pixel belongs to the informative region) the equalizer determines a type of the biological material represented by the corresponding pixel value (for example, blood, muscle, fat and so on depending on the color of the pixel value), and then adds its optical value (for example, ranging from 0 to 1 depending on the type of biological material and on a brightness of the pixel value) to the corresponding cell of the reflectance equalization map, whereas if the corresponding label in the reflectance segmentation mask is deasserted (meaning that the pixel belongs to the non-informative region) the equalizer adds a null value to the corresponding cell of the reflectance equalization map. The adapter at block 428 retrieves the reflectance segmentation mask and the reflectance equalization map just added to the corresponding repositories and optionally adapts them to the corresponding fluorescence image (from the corresponding repository). For example, the adapter may down-scale/up-scale the reflectance segmentation mask and the reflectance equalization map to adapt them to the fluorescence image when they have different sizes (for example, with low-pass filtering followed by sub-sampling or with interpolation followed by low-pass filtering, respectively). In any case, the adapter adds the fluorescence segmentation mask and the fluorescence equalization map (equal to the reflectance segmentation mask and to the reflectance equalization map, respectively, possibly adapted to the fluorescence image) to the corresponding repositories.

Referring back to the block 412, if the entry just added to the prepared reflectance image repository contains the null value, the process instead descends into block 430. In this case, the adapter estimates the fluorescence segmentation mask and the fluorescence equalization map corresponding to the missing (prepared) reflectance image according to one or more preceding fluorescence segmentation masks and fluorescence equalization maps, respectively (extracted from the corresponding repositories). For example, each of the fluorescence segmentation mask and the fluorescence equalization map is simply set equal to the preceding one or it is calculated by interpolating two or more preceding ones. As above, the adapter adds the fluorescence segmentation mask and the fluorescence equalization map so obtained to the corresponding repositories.

In any case, the flow of activity again merges at block 432 from the block 428 or the block 430. At this point, the processor retrieves the fluorescence segmentation mask and the fluorescence equalization map just added to their repositories and the corresponding fluorescence image from its repository for (post-)processing the fluorescence image limited to its informative region (and possibly limited to its non-informative region as well). For example, first of all the processor optionally equalizes the fluorescence image (limited to its informative region) according to the corresponding optical properties of the reflectance image. For this purpose, the equalizer takes each pixel of the fluorescence image into account; if the corresponding label in the fluorescence segmentation mask is asserted (meaning that the pixel belongs to the informative region) the equalizer updates its pixel value according to the corresponding optical value in the fluorescence equalization map (for example, by increasing it when the optical value indicates that the corresponding biological material, such as blood, significantly shields the fluorescence light). In this way, it is possible to compensate the effects of the different biological materials on the fluorescence light that is acquired; particularly, the limitation of this operation to the informative region only avoids that the foreign objects might adversely affect its result. The flow of activity branches at block 434 according to the type of processing to be applied to the (possibly equalized) fluorescence image. Particularly, in case of auto-scaling the blocks 436-446 are executed, whereas in case of thresholding the blocks 448-464 are executed. In both cases, the flow of activity merges again at block 466.

With reference now to the block 436 (auto-scaling), the processor determines an (informative) fluorescence range of the informative region as the difference between its highest pixel value and its lowest pixel value and a (non-informative) fluorescence range of the non-informative region as the difference between its highest pixel value and its lowest pixel value. The informative fluorescence range and a pre-defined display range of the monitor (retrieved from a corresponding configuration variable) are used as parameters of a pre-defined parametric function (for example, of logarithmic type) to obtain a corresponding informative mapping function; likewise, the non-informative fluorescence range and the display range are used as parameters of a pre-defined parametric function (either the same or different with respect to above, such as with the addition of a scaling factor to mask the content of the non-informative region) to obtain a corresponding non-informative mapping function. A loop is then entered for auto-scaling the informative region and the non-informative region separately. The loop begins at block 438, wherein the processor takes a (current) pixel of the fluorescence image into account (starting from a first one in any arbitrary order). The process branches at block 440 according to the corresponding label in the fluorescence segmentation mask. If the label is asserted (meaning that the pixel belongs to the informative region), the processor at block 442 converts the corresponding pixel value by applying the informative mapping function and adds it to the same cell of a (new) auto-scaled fluorescence image (in a corresponding temporary variable). Conversely, if the label is deasserted (meaning that the pixel belongs to the non-informative region), the processor at block 444 converts the corresponding pixel value by applying the non-informative mapping function and adds it to the same cell of the auto-scaled fluorescence image. In both cases, the processor at block 446 verifies whether a last pixel of the fluorescence image has been processed. If not, the process returns to the block 438 to repeat the same operations on a next pixel. Conversely (once all the pixels have been processed), the loop is exit by descending into the block 466.

With reference instead to the block 448 (thresholding), the processor determines a threshold value using only the pixel values of the informative region (for example, by applying the Otsu's algorithm thereto). A loop is then entered for thresholding the informative region. The loop begins at block 450, wherein the processor takes a (current) pixel of the fluorescence image into account (starting from a first one in any arbitrary order). The process branches at block 452 according to the corresponding label in the fluorescence segmentation mask. If the label is asserted (meaning that the pixel belongs to the informative region), the processor at block 454 compares the corresponding pixel value with the threshold value. If the pixel value is (possibly strictly) higher than the threshold value (i.e., it belongs to the target segment), the processor at block 456 copies it to the same cell of a (new) thresholded fluorescence image (in a corresponding temporary variable). Conversely, if the pixel value is (possibly strictly) lower than the threshold value (i.e., it belongs to the non-target segment), the processor at block 458 resets the pixel value in the same cell of the thresholded fluorescence image to zero (so as to mask it). The same point is also reached from the block 452 if the label is deasserted (meaning that the pixel belongs to the non-informative region). In any case, the process continues to block 460 from either the block 456 or the block 458. At this point, the processor verifies whether a last pixel of the fluorescence image has been processed. If not, the process returns to the block 450 to repeat the same operations on a next pixel. Conversely (once all the pixels have been processed), the loop is exit by descending into block 462. Alternatively, the processor creates a thresholding mask (formed by a matrix of cells with the same size as the fluorescence images, each storing a flag); for each pixel value of the fluorescence image, the processor asserts the corresponding flag (for example, to the value 1) if both the corresponding label in the fluorescence segmentation mask is asserted and the pixel value is (possibly strictly) higher than the threshold value or it deasserts the corresponding flag (for example, to the value 0) otherwise. With reference now to the block 462, the processor may further process the thresholded fluorescence image so obtained. For example, the processor calculates one or more (target) statistical parameters of the target segment and one or more (non-target) statistical parameters of the non-target segment of the thresholded fluorescence image (for example, their average and standard deviation). For this purpose, considering the case with the thresholding mask (with similar considerations that apply otherwise), the processor takes each pixel of the fluorescence image into account; if the corresponding flag in the thresholding mask is asserted (meaning that the pixel belongs to the target segment) the processor uses the corresponding pixel value for incrementing the calculation of the target statistical parameters, whereas if the corresponding flag in the thresholding mask is deasserted and the label in the fluorescence segmentation mask is asserted (meaning that the pixel belongs to the non-target segment) the processor uses the corresponding pixel value for incrementing the calculation of the non-target statistical parameters. The processor at block 464 updates the pixel values of the target segment according to the target statistical parameters, to the non-target statistical parameters or to both of them. For this purpose, the processor takes each pixel of the thresholded fluorescence image into account; for example, if the corresponding flag in the thresholding mask is asserted (meaning that the pixel belongs to the target segment), the processor subtracts the average of the non-target segment from the corresponding pixel value, divides the obtained result or the (original) pixel value by the standard deviation of the target segment, by the standard deviation of the non-target segment, by a combination of them (such as their sum, difference, average and the like) and so on. The process then descends into the block 466.

With reference now to the block 466, the processor adds the processed fluorescence image so obtained to the corresponding repository (and the possible corresponding thresholding mask to another repository). The visualizer at block 468 retrieves the processed fluorescence image just added to the corresponding repository and optionally the corresponding fluorescence segmentation mask and reflectance image (and the possible corresponding thresholding mask) from their repositories. The visualizer generates the corresponding output image (based on the processed fluorescence image) and adds it to the corresponding repository. For example, the visualizer may set the output image simply equal to the processed fluorescence image alone (in case of the thresholding mask, the same result is achieved by masking the pixel values of the fluorescence image whose corresponding flags in the thresholding mask are deasserted). In addition or in alternative, the visualizer (after re-scaling the processed fluorescence image or the reflectance image if necessary to equalize their sizes) may generate a combined image given by the pixel values of the processed fluorescence image and of the reflectance image in the informative region and in the non-informative region, respectively, or an overlaid image given by the pixel values of the processed fluorescence image higher than zero (or whose flag in the thresholding mask is asserted) and of the reflectance image otherwise. In any case, the monitor drive at block 470 displays the output image just added to the corresponding repository. In this way, the output images are displayed substantially in real-time with the acquisition of the corresponding fluorescence/reflectance images, apart from a short delay due to their generation.

With reference now to the block 472, if the imaging process is still in progress, the flow of activity returns before the blocks 406-408 to repeat the same operations continually. Conversely, if the imaging process has ended, as indicated by an end command entered into the imaging system by the operator (for example, with its keyboard), the process ends at the concentric white/black stop circles 474 (after turning off the excitation light source and the white light source via the corresponding drives).

Moving to FIG. 5, its activity diagram represents an exemplary process that may be used to configure the segmenter with a method 500 (during a development of the imagining system and possibly during next validations thereof). The process is executed on a configuration (computing) system, for example, a personal computer (comprising as above one or more microprocessors, a non-volatile memory, a volatile memory, a mass-memory and controllers for its peripherals). For this purpose, the configuration system comprises the following software components. A configurator is used to configure the segmenter. The configurator accesses (in read/write mode) a reflectance image repository storing a plurality of (image) sequences of (reference) reflectance images and it accesses (in read/write mode) a reflectance segmentation mask repository storing corresponding (sample) reflectance segmentation masks.

The process begins at the black start circle 503 and then passes to block 506, wherein the configurator uploads (for example, via removable storage units or the communication network) multiples image sequences of reflectance images, acquired as above during different (sample) surgical procedures via corresponding imaging systems (for example, some hundreds of image sequences each of several tens of reflectance images), and adds them to the corresponding repository. Continuing to block 509, each reflectance image is segmented manually into its (reflectance) informative region and (reflectance) non-informative region. For example, this result is achieved with a semi-automatic approach, wherein a preliminary segmentation is performed automatically (for example, by applying the Simple Interactive Object eXtraction (SIOX) algorithm) and the obtained result is refined manually to correct possible errors. The reflectance segmentation masks so obtained are then added to the corresponding repository.

The configurator at block 512 selects a training set, which is formed by part of the (image/mask) pairs of reflectance image and corresponding reflectance segmentation mask that are available. For example, the training set is defined by sampling the available image/mask pairs randomly indiscriminately among all of them (so that the longer the image sequences, the higher their sampling frequency) or homogeneously in the image sequences (so that a same number of image/mask pairs is provided for each image sequence). The flow of activity then branches at block 515 according to the implementation of the segmenter. Particularly, when the segmenter is based on a classification algorithm the blocks 518-521 are executed, whereas when the segmenter is based on a deep learning technique the block 524 is executed.

With reference now to the block 518 (classification algorithm), the configurator performs a features selection step for determining an (optimized) set of features that optimizes the performance of the segmenter among a high number of possible (candidate) features. For example, the features selection step is based on a wrapper method wherein the optimized set is determined with an iterative optimization of the classification algorithm. For this purpose, a brute force approach is at first applied to initialize the optimized set. In order to make the computational complexity of the operation feasible in practice, the initialization of the optimized set is limited to a maximum size of a few units (for example, ≤3) and a simplified version of the classification algorithm is used (for example, in case of the CRF algorithm, it is limited to the node potential with a default model, such as based on the Naïve Bayes algorithm). For this purpose, the configurator takes into account every (feature) combination of the candidate features formed by a number of them at most equal to the maximum size. For each feature combination, the configurator causes the segmenter to calculate the reflectance segmentation masks corresponding to the reflectance images of the training set by applying the classification algorithm with this feature combination. The configurator calculates a quality index indicative of a quality of the segmentation provided by the feature combination. For this purpose, the configurator calculates a similarity index measuring a similarity between each (calculated) reflectance segmentation mask so obtained and the corresponding (reference) reflectance segmentation mask in the training set; for example, the similarity index is defined by the Sorensen-Dice coefficient, as twice the number of pixels having the same label in the calculated/reference reflectance segmentation masks divided by the total number of pixels (ranging from 0 to 1 in increasing order of similarity), or by the Jaccard, Bray-Curtis, Czekanowski, Steinhaus, Pielou, Hellinger and so on index. The segmenter then calculates the quality index as an average of the similarity indexes of all the calculated reflectance segmentation masks with respect to the corresponding reference reflectance segmentation masks. The optimized set is initialized to the feature combination providing the highest quality index. The configurator then applies a step-wise approach to expand the optimized set. For this purpose, the configurator takes into account every additional candidate feature not already comprised in the optimized set. For each additional (candidate) feature, the configurator causes the segmenter to calculate the reflectance segmentation masks corresponding to the reflectance images of the training set by applying the classification algorithm with the features of the optimized set plus this additional feature and it calculates the corresponding quality index as above. If the (best) additional feature, providing the highest quality index when added to the optimized set, involves a significant improvement (for example, a difference between the quality index of the optimized set plus the best additional feature and the quality index of the (original) optimized set is (possibly strictly) higher than a minimum values, such as 5-10%), the configurator adds the best additional feature to the optimized set. The same operations are repeated until an acceptable quality index is obtained, the best additional feature does not provide any significant improvement or the optimized set has reached a maximum allowable size (for example, 10-15). The configurator at block 521 optionally selects one or more operative parameters of the classification algorithm that optimize the performance of the segmenter. For example, in the case of the CRF algorithm, this involves the selection of an optimized node model and an optimized edge model for computing the node potentials and the edge potentials, respectively, and of optimized values of their (node) model parameters and (edge) model parameters, respectively. In order to make the computational complexity of the operation feasible in practice, the selection of the optimized node/edge models is performed with an empirical approach independently of the feature selection step (i.e., by using the optimized set determined above). For example, at first the configurator selects the optimized node model among a plurality of possible (candidate) node models (for example, based on the Naïve Bayes, Gaussian Mixture Models, k-Nearest Neighbors, Artificial Neural Networks, Support Vector Machines and similar algorithms) by keeping the edge model fixed to a default one (for example, the Potts model) and using default values of the node/edge model parameters. For this purpose, for each candidate node model, the configurator causes the segmenter to calculate the reflectance segmentation masks corresponding to the reflectance images of the training set by applying the classification algorithm with this candidate node model and it calculates the corresponding quality index as above. The configurator sets the optimized node model to the candidate node model providing the highest quality index. Later on, the configurator selects (for the classification algorithm with the above-determined optimized node model) the optimized edge model among a plurality of possible (candidate) edge models (for example, based on the Potts, Contrast Sensitive Potts, Contrast-sensitive Potts model with prior probability and similar algorithms) with default values of the node/edge model parameters. For this purpose, for each candidate edge model, the configurator causes the segmenter to calculate the reflectance segmentation masks corresponding to the reflectance images of the training set by applying the classification algorithm with this candidate edge model and it calculates the corresponding quality index as above. The configurator sets the optimized edge model to the candidate edge model providing the highest quality index. In the end, the configurator searches the optimized values of the node/edge model parameters for the above-determined optimized node model and optimized edge model. For this purpose, the configurator causes the segmenter to calculate the reflectance segmentation masks corresponding to the reflectance images of the training set by applying the classification algorithm with the optimized node/edge models and varying model parameters thereof and it calculates the corresponding quality indexes as above. The operations are driven by an optimization method (for example, with the Powell search algorithm) until an acceptable quality index is obtained.

With reference instead to the block 524 (deep learning) the configurator performs a training step of the neural network of the segmenter with the training set, in order to find (optimized) values of its weights that optimize the performance of the segmenter. In order to make the computational complexity of the operation feasible in practice, the training step is based on an iterative process, for example, based on the Stochastic Gradient Descent (SGD) algorithm. For this purpose, at the beginning the configurator initializes the weights of the neural network (for example, randomly). The configurator inputs the reflectance images of the training set to the neural network to obtain the corresponding reflectance segmentation masks and it calculates the corresponding quality index as above. The configurator determines a change of the weights that should improve the performance of the neural network; particularly, in the SGD algorithm the direction and the amount of the change is given by a gradient of an error function with respect to the weights, which is approximated with a back-propagation algorithm. The same operations are repeated until an acceptable quality index is obtained or the change of the weights do not provide any significant improvement (meaning that a minimum, at least local, or a flat region of the error function has been found). The weights may be changed either in an iterative mode (after obtaining every reflectance segmentation mask) or in a batch mode (after obtaining all the reflectance segmentation masks). In any case, the weights are changed with the addition of a random noise and/or the training step is repeated starting with one or more different initializations of the neural network to find different (and possibly better) local minimums and to discriminate the flat regions of the error function. In this way, the features to be used for segmenting the reflectance images (implicitly defined by the weights) are determined automatically during the training step, without any need of their explicit selection.

In both cases, the flow of activity again merges at block 527 from the block 521 or the block 524. At this point, the configurator selects a test set, which is formed by part of the image/mask pairs defined by sampling the available image/mask pairs randomly indiscriminately among all of them or homogeneously in the image sequences. The configurator at block 530 causes the segmenter so obtained to calculate the reflectance segmentation masks corresponding to the reflectance images of the test set, and it calculates the corresponding quality index as above. The flow of activity branches at block 533 according to the quality index. If the quality index is (possibly strictly) lower than an acceptable value, this means that the capability of generalization of the segmenter (from its configuration based on the learning set to the test set) is too poor; in this case, the process returns to the block 512 to repeat the same operations with a different training set (or to block 506 to augment the image sequences of reflectance images, not shown in the figure). Conversely, if the quality index is (possibly strictly) higher than the acceptable value, this means that the capability of generalization of the segmenter is satisfactory; in this case, the configurator at block 536 accepts the configuration of the segmenter and deploys it to a batch of imaging systems. The process then ends at the concentric white/black stop circles 539.

MODIFICATIONS

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof, conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. Moreover, items presented in a same group and different embodiments, examples or alternatives are not to be construed as de facto equivalent to each other (but they are separate and autonomous entities). In any case, each numerical value should be read as modified according to applicable tolerances; particularly, unless otherwise indicated, the terms "substantially", "about", "approximately" and the like should be understood as within 10%, preferably 5% and still more preferably 1%. Moreover, each range of numerical values should be intended as expressly specifying any possible number along the *continuum* within the range (comprising its end points). Ordinal or other qualifiers are merely used as labels to distinguish elements with the same name but do not by themselves connote any priority, precedence or order. The terms include, comprise, have, contain, involve and the like should be intended with an open, non-exhaustive meaning (i.e., not limited to the recited items), the terms based on, dependent on, according to, function of and the like should be intended as a non-exclusive relationship (i.e., with possible further variables involved), the term a/an should be intended as one or more items (unless expressly indicated otherwise), and the term means for (or any means-plus-function formulation) should be intended as any structure adapted to or configured for carrying out the relevant function.

For example, an embodiment provides a method for assisting a medical procedure on a patient. However, the method may be used for assisting any medical procedure (for example, a surgical procedure, a diagnostic procedure, a therapeutic procedure and so on) on any patient (for example, a human being, an animal, and so on); moreover, the corresponding steps may be performed in any way (for example, continually during the medical procedure, upon request and so on). In any case, although the method may facilitate the task of a physician, it remains a data-processing method only providing information that may help the physician but with the medical activity *stricto* sensu that is always made by the physician himself/herself.

In an embodiment, the method comprises the following steps under the control of a computing device. However, the computing device may be of any type (see below).

In an embodiment, the method comprises acquiring (by the computing device) a luminescence image of a field of view. However, the luminescence image may be acquired in any way (for example, with any frequency, any excitation light, acquired directly by controlling any acquisition unit, transferred with a removable storage unit, uploaded via a network and so).

In an embodiment, the field of view contains a region of interest (for the medical procedure) of the patient. However, the region of interest may be of any type (for example, a surgical cavity of a surgical procedure, an interior cavity of an endoscopic procedure, either of open type accessed via a hollow or of closed type accessed via an incision, and so on).

In an embodiment, the region of interest comprises at least one target body of the medical procedure. However, the target bodies may be in any number and of any type (for example, lesions, such as tumors, polyps, inflammations, thrombi and the like, to be resected, identified, monitored or treated, body-parts to be repaired, such as a bleeding vessel to be cauterized, a narrow esophagus to be widened and the like, structures surrounding any item on which the physician should act, and so on).

In an embodiment, the target body contains a luminescence substance. However, the luminescence substance may be of any extrinsic/intrinsic or exogenous/endogenous type (for example, any luminescence agent, any natural luminescence component, based on any luminescence phenomenon, such as fluorescence, phosphorescence, chemiluminescence, bio-luminescence, induced Raman-radiation, and so on).

In an embodiment, the field of view comprises one or more foreign objects different from the region of interest. However, the foreign objects may be in any number and of any type (for example, instruments, hands, tools, body-parts, background materials and so on).

In an embodiment, the luminescence image comprises a plurality of luminescence values representative of a luminescence light being emitted by the luminescence substance at corresponding luminescence locations of the field of view. However, the luminescence image may have any size and shape (from a whole matrix to one or more portions thereof) and it may comprise luminescence values of any type and for any luminescence locations (for example, gray-scale or colors values in RBG, YcBcr, HSL, CIE-L*a*b, Lab color and the like representation, for pixels, voxels, groups thereof and so on); the luminescence light may be of any type (for example, NIR, Infra-Red (IR), visible and so on) and it may be emitted in any way (for example, in response to a corresponding excitation light or more generally to any other excitation different from heating).

In an embodiment, the method comprises acquiring (by the computing device) an auxiliary image of the field of view. However, the auxiliary image may be acquired in any way (for example, either the same or different with respect to the luminescence image, concurrently with the luminescence image or in short succession, and so on).

In an embodiment, the auxiliary image comprises a plurality of auxiliary values representative of an auxiliary light (different from the luminescence light) being received from corresponding auxiliary locations of the field of view. However, the auxiliary image may have any size and shape and it may comprise auxiliary values of any type and for any auxiliary locations (either the same or different with respect to the luminescence image); the auxiliary light may be of any type different from the luminescence light of the luminescence image (for example, visible light, IR light, Ultra-Violet (UV) light, other luminescence light at different wavelength and so on).

In an embodiment, the method comprises identifying (by the computing device) an auxiliary informative region of the auxiliary image representative of the region of interest without the foreign objects according a content of the auxiliary image. However, the auxiliary informative region may be of any type (for example, a single area, one or more disjoint areas, defined by a corresponding mask or directly in the auxiliary image, and so on) and it may be identified in any way (for example, by segmenting the auxiliary image semantically/non-semantically into the informative region and the non-informative region, by searching the informative region in the auxiliary image and so on).

In an embodiment, the method comprises identifying (by the computing device) a luminescence informative region of the luminescence image corresponding to the auxiliary informative region. However, the luminescence informative region may be identified in any way (for example, by transferring the identification of the auxiliary informative region directly or with any adaptation, and so on). Moreover, this operation may be performed indiscriminately or it may be conditioned on a quality of the identification of the auxiliary informative region; for example, it is possible to calculate a quality metric (of the whole process or of a step thereof) and to assign all the luminescence locations to the luminescence informative region if the quality metric does not reach a corresponding threshold.

In an embodiment, the method comprises generating (by the computing device) a processed luminescence image. However, the processed luminescence image may be of any type (for example, an auto-scaled fluorescence image, a thresholded fluorescence image, a segmented fluorescence image and so on).

In an embodiment, the processed luminescence image is generated by processing the luminescence image limited to the luminescence informative region. However, this result may be achieved in any way (for example, by processing the informative luminescence region and the non-informative luminescence region separately, with either the same or different operations, by processing the informative luminescence region only, with the non-informative luminescence region that is left unchanged, is darkened, is cancelled and the like, and so on).

In an embodiment, the processing of the luminescence image is based on the luminescence values of the luminescence informative region for facilitating an identification of a representation of the target body therein. However, the processing may be based on these luminescence values in any way (for example, on their distribution, range, probability and so on) to achieve this result in any way (for example, by making the representation of the target body more conspicuous for its manual identification, by identifying the representation of the target body automatically and so on).

In an embodiment, the method comprises outputting (by the computing device) an output image based on the processed luminescence image. However, the output image may be of any type (for example, the same processed luminescence image, the processed luminescence image combined/overlaid with the reflectance image, and so on) and it may be output in any way (for example, displayed, printed, transmitted remotely, in real-time or off-line, and so on).

Further embodiments provide additional advantageous features, which may however be omitted at all in a basic implementation.

Particularly, in an embodiment the method is for assisting a surgical procedure on the patient. However, the surgical procedure may be of any type (for example, for curative purposes, for prevention purposes, for aesthetic purposes in standard surgery, minimally invasive surgery, such as laparoscopy, arthroscopy, angioplasty, and so on).

In an embodiment, said step of outputting the output image comprises displaying (by the computing device) the output image substantially in real-time with said step of acquiring the luminescence image. However, the output image may be displayed in any way (for example, on any display unit such as a monitor, virtual reality glasses and the like, with any delay due to its generation, and so on).

In an embodiment, the region of interest is a surgical cavity of the patient. However, the surgical cavity may be of any type (for example, a wound, an open-body and so on).

In an embodiment, at least part of the foreign objects overlaps the region of interest. However, the foreign objects may be arranged at any position (for example, overlapping the region on interest to any extent, surrounding it, spaced apart from it, any combination thereof and so on).

In an embodiment, the foreign objects comprise one or more medical instruments, one or more hands, one or more medical tools, one or more body-parts of the patient not of interest for the medical procedure and/or one or more background materials. However, the foreign objects may comprise any number and type of medical instruments (for example, surgical instruments like a scalpel, scissors, endoscopic instruments like a manipulator, a sampling device, a polypectomy snare, and so on), hands (for example, of a surgeon, an assistant, a nurse and so on), medical tools (such as surgical tools like a gauze, a retractor, a drape, a cover, endoscopic tools like a hemostatic clip, an irrigator, and so on), body-parts being not of interest (such as body-parts surrounding the region of interest, like skin around the surgical cavity, muscles, organs that are irrelevant for the medical procedure, such as the liver, and so on), background materials (such as an operating table, walls, floor and so on) or more generally partial, different and additional ones (for example, biological material of the patient disturbing the medical procedure, such as fecal residuals in colonoscopy, food residuals in gastroscopy, and so on).

In an embodiment, the auxiliary image is a reflectance image, the auxiliary light is a visible light and the auxiliary values are representative of the visible light being reflected by the corresponding auxiliary locations of the field of view illuminated by a white light. However, the white light (and the corresponding visible light) may be of any type (for example, any non-luminescence light that causes no significant luminescence phenomenon to the luminescence substance).

In an embodiment, the luminescence substance is a luminescence agent that has been pre-administered to the patient before performing the method. However, the luminescence agent may be of any type (for example, any targeted luminescence agent, such as based on specific or non-specific interactions, any non-targeted luminescence agent, and so on) and it may have been pre-administered in any way (for example, with a syringe, an infusion pump, and so on) and at any time (for example, in advance, immediately before performing the method, continuously during it, and so on). In any case, this is a data-processing method that may be implemented independently of any interaction with the patient; moreover, the luminescence agent may also be administered to the patient in a non-invasive manner (for example, orally for imaging the gastrointestinal tract, via a nebulizer into the airways, via topical spray application or topical introduction during the medical procedure, and so on), or in any case without any substantial physical intervention on the patient that would require professional medical expertise or entail any health risk for him/her (for example, intramuscularly).

In an embodiment, said step of identifying the auxiliary informative region comprises segmenting (by the computing device) the auxiliary image semantically. However, the auxiliary image may be segmented semantically in any way (for example, with a classification algorithm, a neural network and so on).

In an embodiment, the auxiliary image is segmented semantically into the auxiliary informative region corresponding to at least one region of interest class of the region of interest and an auxiliary non-informative region corresponding to one or more foreign objects classes of the foreign objects. However, the region of interest class and the foreign objects classes may be in any number and of any type (for example, a single region of interest class for the whole region of interest, a single foreign object class for all the foreign objects, multiple region of interest classes for corresponding parts of the region of interest or groups thereof, multiple foreign object classes for corresponding types of foreign objects or groups thereof, and so on).

In an embodiment, said step of segmenting the auxiliary image comprises segmenting (by the computing device) the auxiliary image semantically with a neural network. However, the neural network may be of any type (for example, U-Net, Convolutional Neural Network, Feedforward Neural Network, Radial Basis Function Neural Network, Recurrent Neural Network, Modular Neural Network and so on). The neural network may have been trained in any way (for example, based on the Stochastic Gradient Descent, the Real-Time Recurrent Learning, the Higher-order gradient descent techniques, the Extended Kalman-filtering and similar algorithms) with any number and type of training pairs (for example, selected randomly, homogenously and so on).

In an embodiment, said step of segmenting the auxiliary image comprises determining (by the computing device) one or more feature maps for corresponding features of the auxiliary image. However, the features may be in any number and of any type (for example, selected with any heuristic, iterative, filtering and so on method among partial, different and additional candidate features with respect to above).

In an embodiment, each of the feature maps comprises corresponding feature values of the auxiliary locations. However, the feature values may be determined in any way (for example, with any filters, neural networks, encoders, redactors and so on).

In an embodiment, the method comprises segmenting (by the computing device) the auxiliary image semantically by applying a classification algorithm to the feature values of the feature maps. However, the classification algorithm may be of any type (for example, Conditional Random Field, Markov Random Fields, SIOX, GrabCut, decision trees, k-nearest neighbors and so on). The classification algorithm may be configured in any way (for example, with any heuristic, iterative, filtering and so on method for any parameters thereof).

In an embodiment, said step of identifying the auxiliary informative region comprises, when the auxiliary image comprises one or more disconnected portions completely surrounded by the auxiliary informative region, assigning (by the computing device) the disconnected portions to the auxiliary informative region. However, this fill-hole step may be performed in any way (for example, indiscriminately or only for disconnected portions larger than a threshold, for either the classification algorithms or the deep learning techniques, to the auxiliary image or to the luminescence image, and so no).

In an embodiment, the method comprises pre-processing (by the computing device) the auxiliary image before said identifying the auxiliary informative region. However, the auxiliary image may be subject to any number and type of pre-processing steps (partial, different and additional ones with respect to above), down to none at all.

In an embodiment, the method comprises pre-processing (by the computing device) the auxiliary image before the segmentation thereof by applying a histogram equalization to the auxiliary image. However, this histogram equalization may be performed in any way (for example, with ordinary histogram equalization, adaptive histogram equalization, contrastive limited adaptive equalization and similar algorithms).

In an embodiment, the histogram equalization is performed in response to a brightness indicator of the auxiliary image being comprised between a darkness threshold (indicative of a feasibility of said identifying the auxiliary informative region) and a brightness threshold (higher than the darkness threshold). However, the brightness indicator may be calculated in any way (for example, as the mean, modal, median and on so) and the darkness/brightness threshold may have any value (for example, pre-defined, determined dynamically and so on); in any case, the possibility is not excluded of performing the histogram equalization indiscriminately (always) or never.

In an embodiment, said step of identifying the auxiliary informative region comprises identifying (by the computing device) the auxiliary informative region further according to the luminescence image. However, the luminescence image may be used in any way to identify the auxiliary informative region (for example, by inputting the luminescence image as well to the neural network, by extracting one or more additional feature maps from the luminescence image for use by the classification algorithm, either directly or weighted to limit the impact of the luminescence image, and so on).

In an embodiment, said step of generating the processed luminescence image comprises auto-scaling (by the computing device) the luminescence informative region according to the luminescence values of the luminescence informative region. However, the luminescence informative region may be auto-scaled in any way (for example, to map, log-compress, saturate and so on its luminescence values).

In an embodiment, said step of auto-scaling the luminescence informative region comprises determining (by the computing device) a luminescence range of the luminescence values of the luminescence informative region. However, the luminescence range may be determined in any way (for example, indiscriminately, by disregarding outliers, and so on).

In an embodiment, said step of auto-scaling the luminescence informative region comprises converting (by the computing device) the luminescence values of the luminescence informative region according to a mapping function mapping the luminescence range to a display range for displaying the luminescence image. However, the mapping function may be of any type (for example, non-linear, such as logarithmic, exponential and the like, linear and so on).

In an embodiment, said step of generating the processed luminescence image comprises thresholding (by the computing device) the luminescence informative region according to the luminescence values of the luminescence informative region thereby partitioning the luminescence informative region into a target segment representative of the target body and a non-target segment representative of a rest of the region of interest different from the target body. However, the luminescence informative region may be thresholded in any way (for example, based on statistical distribution, entropy, clustering or object attributes, of binary, multilevel or multiband type, and so on).

In an embodiment, said step of outputting the output image comprises outputting (by the computing device) the output image by highlighting the target segment with respect to the non-target segment. However, the target segment may be highlighted in any way (for example, by masking the non-target segment, by representing the target segment in color and the non-target segment in black-and-white, by increasing and/or reducing a luminosity of the target segment and of the non-target segment, respectively, and so on).

In an embodiment, said step of thresholding the luminescence informative region comprises determining (by the computing device) a threshold value according to a statistical distribution of the luminescence values of the luminescence informative region. However, the threshold value may be determined in any way (for example, working on bimodal, unimodal, multimodal and so on statistical distributions).

In an embodiment, said step of thresholding the luminescence informative region comprises assigning (by the computing device) each of the luminescence locations of the luminescence informative region to the target segment or to the non-target segment according to a comparison of the corresponding luminescence value with the threshold value. However, the luminescence locations may be assigned to the target/non-target segments according to the threshold value in any way (for example, when they are higher and/or lower, by generating a thresholded luminescence image or a thresholding mask, and so on).

In an embodiment, said step of thresholding the luminescence informative region comprises calculating (by the computing device) one or more target statistical parameters of the luminescence values of the target segment and/or one or more non-target statistical parameters of the non-target segment. However, the target/non-target statistical parameters may be in any number, down to none for each one of them, and of any type, either the same or different (for example, mean, median, mode, standard deviation, variance, skewness and so on).

In an embodiment, said step of generating the processed luminescence image comprises updating (by the computing device) the luminescence values of the target segment each according to the target statistical parameters and/or the non-target statistical parameters. However, the target segment may be processed in any way according to these statistical parameters (for example, only according to the target statistical parameters, only according to the non-target statistical parameters, according to both of them, with partial, different and additional processing with respect to the ones mentioned above, either individually or in any combination thereof, and so on).

In an embodiment, the method comprises determining (by the computing device) corresponding optical values (of at least one optical parameter relating to the luminescence light) for the auxiliary locations of the auxiliary image limited to the auxiliary informative region according to a content thereof. However, the optical parameters may be in any number and of any type (for example, partial, different and additional optical parameters with respect to the ones mentioned above, and so on) and the corresponding optical values may be determined in any way (for example, individually according to the corresponding auxiliary values, by applying any classification algorithm and so on).

In an embodiment, said step of generating the processed luminescence image comprises equalizing (by the computing device) the luminescence values of the luminescence informative region according to the optical values. However, the luminescence informative region may be equalized at any time (for example, before and/or after auto-scaling/threshold it, and so on) and in any way (for example, by equalizing each luminescence value only according to the optical value of the corresponding auxiliary location, further according to the optical values of its neighboring auxiliary locations, with partial, different and additional further processing with respect to the ones mentioned above, either individually or in any combination thereof, and so on).

In an embodiment, the luminescence substance is a fluorescence substance (with the luminescence image being a fluorescence image and the luminescence values being representative of a fluorescence light emitted by the fluorescence substance at the corresponding luminescence locations illuminated by an excitation light thereof). However, the fluorescence substance may be of any extrinsic/intrinsic or exogenous/endogenous type (for example, for imaging any pathological tissue, any healthy tissue and so on).

Generally, similar considerations apply if the same solution is implemented with an equivalent method (by using similar steps with the same functions of more steps or portions thereof, removing some steps being non-essential, or adding further optional steps); moreover, the steps may be performed in a different order, concurrently or in an interleaved way (at least in part).

An embodiment provides a computer program, which is configured for causing a computing device to perform the above-mentioned method when the computer program is executed on the computing device. An embodiment provides a computer program product, which comprises one or more computer readable storage media having program instructions collectively stored on the readable storage media, the program instructions being loadable by a computing device to cause the computing device to perform the same method. However, the computer program may be implemented as a stand-alone module, as a plug-in for a pre-existing software program (for example, a manager of the imaging system) or even directly in the latter. In any case, similar considerations apply if the computer program is structured in a different way, or if additional modules or functions are provided; likewise, the memory structures may be of other types, or may be replaced with equivalent entities (not necessarily consisting of physical storage media). The computer program may take any form suitable to be used by any computing device (see below), thereby configuring the computing device to perform the desired operations; particularly, the computer program may be in the form of external or resident software, firmware, or microcode (either in object code or in source code, for example, to be compiled or interpreted). Moreover, it is possible to provide the computer program on any computer readable storage medium. The storage medium is any tangible medium (different from transitory signals per se) that may retain and store instructions for use by the computing device. For example, the storage medium may be of the electronic, magnetic, optical, electromagnetic, infrared, or semiconductor type; examples of such storage medium are fixed disks (where the program may be pre-loaded), removable disks, memory keys (for example, of USB type), and the like. The computer program may be downloaded to the computing device from the storage medium or via a network (for example, the Internet, a wide area network and/or a local area network comprising transmission cables, optical fibers, wireless connections, network devices); one or more network adapters in the computing device receive the computer program from the network and forward it for storage into one or more storage devices of the computing device. In any case, the solution according to an embodiment of the present disclosure lends itself to be implemented even with a hardware structure (for example, by electronic circuits integrated in one or more chips of semiconductor material, such as a Field Programmable Gate Array (FPGA) or application-specific integrated circuits), or with a combination of software and hardware suitably programmed or otherwise configured.

An embodiment provides a computing device, which comprises means configured for performing the steps of the above-mentioned method. An embodiment provides a computing device comprising a circuit (i.e., any hardware suitably configured, for example, by software) for performing each step of the same method. However, the computing device may be of any type (for example, a central unit of an imaging system, a separate computer and so on).

An embodiment provides an imaging system. However, the imaging system may be of any type (for example, a guided surgery equipment, an endoscope, a laparoscope and so on).

In an embodiment, the imaging system comprises the computing device of above. However, the computing device may be provided in the imaging system in any way (for example, embedded, connected with any wired/wireless connections and so on).

In an embodiment, the imaging system comprises an illumination unit for applying an excitation light adapted to exciting the luminescence substance to the field of view. However, the illumination unit may be of any type (for example, based on laser, LEDs, UV/halogen/Xenon lamps, providing the white light as well or not, and so on).

In an embodiment, the imaging system comprises an acquisition unit for acquiring the luminescence image and the auxiliary image. However, the acquisition unit may be of any type (for example, based on any number and type of lenses, wave guides, mirrors, CCD, ICCD, EMCCD, CMOS, InGaAs or PMT sensors, and so on).

Generally, similar considerations apply if the computing device and the imaging system each has a different structure or comprises equivalent components, or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

An embodiment provides a medical procedure on a patient comprising the following steps. A field of view containing a region of interest for the medical procedure of the patient, the region of interest comprising at least one target body of the medical procedure containing a luminescence substance, and one or more foreign objects different from the region of interest is imaged according to the above-mentioned method so as to output the output image. The medical procedure is performed with an assistance of the output image. However, the proposed method may find application in any kind of medical procedure (see above).

In an embodiment, the medical procedure comprises administering a luminescence agent containing the luminescence substance to the patient. However, the luminescence agent may be administered in any way (see above), or this step may be omitted at all (in case the luminescence agent is endogenous).

What is claimed is:

1. A method for imaging a region of interest of a patient for a medical procedure performed thereon,
   wherein the method comprises, under the control of a computing device:
   acquiring, by the computing device, a luminescence image of a field of view containing the region of interest, the region of interest comprising at least one target body of the medical procedure containing a luminescence substance, and one or more foreign objects different from the region of interest, the luminescence image comprising a plurality of luminescence values representative of a luminescence light being emitted by the luminescence substance at corresponding luminescence locations of the field of view,
   acquiring, by the computing device, an auxiliary image of the field of view, the auxiliary image comprising a plurality of auxiliary values representative of an auxiliary light, different from the luminescence light, being received from corresponding auxiliary locations of the field of view,
   segmenting, by the computing device, the auxiliary values of the auxiliary image semantically into at least one region of interest class defining an auxiliary informative region representative of the region of interest without the foreign objects and one or more foreign object classes defining a non-informative region representative of the foreign objects,
   identifying, by the computing device, the luminescence values of the luminescence image defining a luminescence informative region corresponding to the auxiliary values of the auxiliary informative region of the auxiliary image,
   generating, by the computing device, a processed luminescence image by processing the luminescence image limited to the luminescence informative region, the processed luminescence image comprising a plurality of processed luminescence values being based on the luminescence values of the luminescence informative region, wherein the processed luminescence image provides a further representation of the target body facilitating an identification thereof, and
   displaying, by the computing device an output image base on the processed luminescence image substantially in real-time with said acquiring the luminescence image.

2. The method according to claim 1, wherein the medical procedure is a surgical procedure.

3. The method according to claim 2, wherein the region of interest is a surgical cavity of the patient.

4. The method according to claim 1, wherein at least part of the foreign objects overlaps the region of interest.

5. The method according to claim 1, wherein the foreign objects comprise one or more medical implements, one or more hands, one or more body-parts of the patient not of interest for the medical procedure and/or background materials.

6. The method according to claim 1, wherein the auxiliary image is a reflectance image, the auxiliary light is a visible light and the auxiliary values are representative of the visible light being reflected by the corresponding auxiliary locations of the field of view illuminated by a white light.

7. The method according to claim 1, wherein the luminescence substance is a luminescence agent being pre-administered to the patient before performing the method.

8. The method according to claim 1, wherein said segmenting the auxiliary values of the auxiliary image comprises:
   segmenting, by the computing device, the auxiliary values of the auxiliary image semantically with a neural network.

9. The method according to claim 1, wherein said segmenting the auxiliary values of the auxiliary image comprises:
   determining, by the computing device, one or more feature maps for corresponding features of the auxiliary values of the auxiliary image, each of the feature maps comprising corresponding feature values of the auxiliary locations, and
   segmenting, by the computing device, the auxiliary values of the auxiliary image semantically by applying a classification algorithm to the feature values of the feature maps.

10. The method according to claim 1, wherein said segmenting the auxiliary values of the auxiliary image comprises, when the auxiliary image comprises one or more disconnected portions completely surrounded by the auxiliary informative region:

assigning, by the computing device, the disconnected portions to the auxiliary informative region.

11. The method according to claim 1, wherein the method comprises:

pre-processing, by the computing device, the auxiliary image before said segmenting the auxiliary values of the auxiliary image by applying a histogram equalization to the auxiliary values of the auxiliary image in response to a brightness indicator of the auxiliary image being comprised between a darkness threshold, indicative of a feasibility of said segmenting the auxiliary values of the auxiliary image, and a brightness threshold, higher than the darkness threshold.

12. The method according to claim 1, wherein said segmenting the auxiliary values of the auxiliary image comprises:

identifying, by the computing device, the auxiliary informative region further according to the luminescence values of the luminescence image.

13. The method according to claim 1, wherein said generating the processed luminescence image comprises:

auto-scaling, by the computing device, the luminescence informative region according to the luminescence values of the luminescence informative region.

14. The method according to claim 13, wherein said auto-scaling the luminescence informative region comprises:

determining, by the computing device, a luminescence range of the luminescence values of the luminescence informative region, and converting, by the computing device, the luminescence values of the luminescence informative region according to a mapping function mapping the luminescence range to a display range for displaying the luminescence image.

15. The method according to claim 1:

wherein said generating the processed luminescence image comprises:

thresholding, by the computing device, the luminescence informative region according to the luminescence values of the luminescence informative region thereby partitioning the luminescence informative region into a target segment representative of the target body and a non-target segment representative of a rest of the region of interest different from the target body, and wherein said displaying the output image comprises:

displaying, by the computing device, the output image by highlighting the target segment with respect to the non-target segment.

16. The method according to claim 15, wherein said thresholding the luminescence informative region comprises:

determining, by the computing device, a threshold value according to a statistical distribution of the luminescence values of the luminescence informative, and assigning, by the computing device, each of the luminescence locations of the luminescence informative region to the target segment or to the non-target segment according to a comparison of the corresponding luminescence value with the threshold value.

17. The method according to claim 15, wherein said thresholding the luminescence informative region comprises:

calculating, by the computing device, one or more target statistical parameters of the luminescence values of the target segment and/or one or more non-target statistical parameters of the luminescence values of the non-target segment, and updating, by the computing device, the luminescence values of the target segment each according to the target statistical parameters and/or the non-target statistical parameters.

18. The method according to claim 1:

wherein the method comprises:

determining, by the computing device, corresponding optical values, of at least one optical parameter relating to the luminescence light, for the auxiliary locations of the auxiliary image limited to the auxiliary informative region according to a content thereof, and wherein said generating the processed luminescence image comprises:

equalizing, by the computing device, the luminescence values of the luminescence informative region according to the optical values.

19. The method according to claim 1, wherein the luminescence substance is a fluorescence substance, the luminescence image being a fluorescence image and the luminescence values being representative of a fluorescence light emitted by the fluorescence substance at the corresponding luminescence locations illuminated by an excitation light thereof.

20. A computer program product comprising one or more non-transitory computer readable storage media having program instructions collectively stored on the readable storage media, the program instructions readable by a computing device to cause the computing device to perform a method for imaging a region of interest of a patient for a medical procedure performed thereon, wherein the method comprises:

acquiring a luminescence image of a field of view containing the region of interest, the region of interest comprising at least one target body of the medical procedure containing a luminescence substance, and one or more foreign objects different from the region of interest, the luminescence image comprising a plurality of luminescence values representative of a luminescence light being emitted by the luminescence substance at corresponding luminescence locations of the field of view, acquiring an auxiliary image of the field of view, the auxiliary image comprising a plurality of auxiliary values representative of an auxiliary light, different from the luminescence light, being received from corresponding auxiliary locations of the field of view, segmenting the auxiliary values of the auxiliary image semantically into at least one region of interest class defining an auxiliary informative region representative of the region of interest without the foreign objects and one or more foreign object classes defining a non-informative region representative of the foreign objects, identifying the luminescence values of the luminescence image defining a luminescence informative region corresponding to the auxiliary values of the auxiliary informative region of the auxiliary image, generating a processed luminescence image by processing the luminescence image limited to the luminescence informative region, the processed luminescence image comprising a plurality of processed luminescence values being based on the luminescence values of the luminescence informative region, wherein the processed luminescence image provides a further representation of the target body facilitating an identification thereof, and displaying an output image based on the processed luminescence image substantially in real-time with said acquiring the luminescence image.

21. A computing device for imaging a region of interest of a patient for a medical procedure performed thereon, wherein the computing device comprises:

a luminescence drive for acquiring a luminescence image of a field of view containing the region of interest, the region of interest comprising at least one target body of the medical procedure containing a luminescence substance, and one or more foreign objects different from the region of interest, the luminescence image comprising a plurality of luminescence values representative of a luminescence light being emitted by the luminescence substance at corresponding luminescence locations of the field of view, an auxiliary drive for acquiring an auxiliary image of the field of view, the auxiliary image comprising a plurality of auxiliary values representative of an auxiliary light, different from the luminescence light, being received from corresponding auxiliary locations of the field of view, a segmenter for segmenting the auxiliary values of the auxiliary image semantically into at least one region of interest class defining an auxiliary informative region representative of the region of interest without the foreign objects and one or more foreign object classes defining a non-informative region representative of the foreign objects, an adapter for identifying the luminescence values of the luminescence image defining a luminescence informative region corresponding to the auxiliary values of the auxiliary informative region of the auxiliary image, a processor for generating a processed luminescence image by processing the luminescence image limited to the luminescence informative region, the processed luminescence image comprising a plurality of processed luminescence values being based on the luminescence values of the luminescence informative region, wherein the processed luminescence image provides a further representation of the target body facilitating an identification thereof, and an output drive for displaying an output image based on the processed luminescence image substantially in real-time with said acquiring the luminescence image.

22. An imaging system comprising:
the computing device of claim 21,
an illumination unit for applying an excitation light adapted to exciting the luminescence substance to the field of view, and
an acquisition unit for acquiring the luminescence image and the auxiliary image.

23. A medical procedure for performing on a patient, the medical procedure comprising:

acquiring, by a computing device, a luminescence image of a field of view containing the region of interest, the region of interest comprising at least one target body of the medical procedure containing a luminescence substance, and one or more foreign objects different from the region of interest, the luminescence image comprising a plurality of luminescence values representative of a luminescence light being emitted by the luminescence substance at corresponding luminescence locations of the field of view, acquiring, by the computing device, an auxiliary image of the field of view, the auxiliary image comprising a plurality of auxiliary values representative of an auxiliary light, different from the luminescence light, being received from corresponding auxiliary locations of the field of view, segmenting, by the computing device, the auxiliary values of the auxiliary image semantically into at least one region of interest class defining an auxiliary informative region representative of the region of interest without the foreign objects and one or more foreign object classes defining a non-informative region representative of the foreign objects, identifying, by the computing device, the luminescence values of the luminescence image defining a luminescence informative region corresponding to the auxiliary values of the auxiliary informative region of the auxiliary image, generating, by the computing device, a processed luminescence image by processing the luminescence image limited to the luminescence informative region, the processed luminescence image comprising a plurality of processed luminescence values being based on the luminescence values of the luminescence informative region, wherein the processed luminescence image provides a further representation of the target body facilitating an identification thereof, displaying, by the computing device, an output image based on the processed luminescence image substantially in real-time with said acquiring the luminescence image, and performing the medical procedure with an assistance of the output image.

24. The medical procedure according to claim 23, wherein the medical procedure comprises:

administering a luminescence agent containing the luminescence substance to the patient.

* * * * *